US010316183B2

(12) United States Patent
Vorst et al.

(10) Patent No.: US 10,316,183 B2
(45) Date of Patent: Jun. 11, 2019

(54) METHOD FOR OPTIMIZING PLASTIC COMPOSITIONS USED IN PACKAGING TO INCREASE SHELF-LIFE OF PERISHABLE PRODUCTS AND A SYSTEM THEREOF

(71) Applicants: Iowa State University Research Foundation, Inc., Ames, IA (US); Cal Poly Corporation, San Luis Obispo, CA (US)

(72) Inventors: Keith Vorst, Madrid, IA (US); John Wyatt Brown, Atascadero, CA (US); Jeffrey E. Danes, San Luis Obispo, CA (US); Greg Curtzwiler, Petal, MS (US)

(73) Assignees: Iowa State University Research Foundation, Inc., Ames, IA (US); Cal Poly Corporation, San Luis Obispo, CA (US)

( * ) Notice: Subject to any disclaimer, the term of this patent is extended or adjusted under 35 U.S.C. 154(b) by 0 days.

(21) Appl. No.: 15/491,201

(22) Filed: Apr. 19, 2017

(65) Prior Publication Data

US 2017/0298219 A1    Oct. 19, 2017

Related U.S. Application Data

(60) Provisional application No. 62/324,790, filed on Apr. 19, 2016.

(51) Int. Cl.
*C08J 3/20* (2006.01)
*C08J 3/00* (2006.01)
(Continued)

(52) U.S. Cl.
CPC .............. *C08L 67/02* (2013.01); *B65D 81/24* (2013.01); *G01N 21/33* (2013.01);
(Continued)

(58) Field of Classification Search
USPC ..................... 523/303, 305; 521/40; 264/920
See application file for complete search history.

(56) References Cited

U.S. PATENT DOCUMENTS

| 2015/0031837 A1* | 1/2015 | Favis | C08L 23/16 |
| | | | 525/211 |
| 2015/0105532 A1* | 4/2015 | Allen | C07C 51/09 |
| | | | 528/305 |
| 2017/0057145 A1* | 3/2017 | Altonen | B29C 45/7646 |

FOREIGN PATENT DOCUMENTS

WO        20130149356        10/2013

OTHER PUBLICATIONS

Adegoroye et al., "Some Inhibitory Effects of Radiation Stress on Tomato Fruit Ripening", J. Sci. Food Agric., vol. 39, pp. 297-302 (1987).

(Continued)

*Primary Examiner* — Tae H Yoon
(74) *Attorney, Agent, or Firm* — Pepper Hamilton LLP

(57) ABSTRACT

The present invention relates to relates to a method of optimizing a plastic composition formed from a plurality of resin feedstocks. A plurality of resin feedstocks are provided. The plurality of resin feedstocks are blended to form the plastic composition. One or more properties of the plastic composition, including radiation absorption, radiation transmission, gas evolution, radiation fluorescence, or melting properties, are measured. The ratio of the plurality of resin feedstocks being blended into the plastic composition is adjusted, based on said measuring, to form an optimized plastic composition. A system for performing the method is also disclosed.

13 Claims, 15 Drawing Sheets

(51) Int. Cl.
| | |
|---|---|
| *C08L 67/02* | (2006.01) |
| *G01N 21/33* | (2006.01) |
| *G01N 21/35* | (2014.01) |
| *G01N 21/62* | (2006.01) |
| *G01N 21/3563* | (2014.01) |
| *B65D 81/24* | (2006.01) |
| *G01N 33/44* | (2006.01) |
| *G01N 25/00* | (2006.01) |
| *G01N 25/48* | (2006.01) |
| *G01N 21/65* | (2006.01) |
| *G01N 21/64* | (2006.01) |
| *G01N 21/84* | (2006.01) |

(52) U.S. Cl.
CPC ....... *G01N 21/3563* (2013.01); *G01N 33/442* (2013.01); *C08L 2205/025* (2013.01); *C08L 2207/20* (2013.01); *G01N 21/65* (2013.01); *G01N 25/4866* (2013.01); *G01N 2021/3595* (2013.01); *G01N 2021/6419* (2013.01); *G01N 2021/6421* (2013.01); *G01N 2021/8416* (2013.01); *G01N 2223/076* (2013.01); *G01N 2223/623* (2013.01); *Y02P 20/582* (2015.11)

(56) References Cited

OTHER PUBLICATIONS

Alba et al., "Fruit-Localized Phytochromes Regulate Lycopene Accumulation Independently of Ethylene Production in Tomato", Plant Physiology, vol. 123, p. 363-370 (2000).
Anttonen et al., "Influence of Fertilization, Mulch Color, Early Forcing, Fruit Order, Planting Date, Shading, Growing Environment, and Genotype on the Contents of Selected Phenolics in Strawberry (Fragaria x ananassa Duch.) Fruits", J. Agric. Food Chem., vol. 54, pp. 2614-2620 (2006).
Botelho et al., Studies on Thermal and Thermo-oxidative Degradation of Poly(ethylene terephthalate) and Poly (butylene terephthalate), Polymer Degradation and Stability, vol. 74, pp. 39-48 (2001).
Cabibel et al., "Evolution de la teneur en carote'noi'des de la tomate en fonction de le maturation et des conditions le culture", Ann. Technol. Agric. vol. 29, pp. 27-45 (1980).
El-Gizawy et al., "Effect of Different Shading Levels on Tomato Plants. 2. Yield and Fruit Quality", Acta Hortic., vol. 323, pp. 349-354 (1992).
Eskling et al., "Changes in the Quantities of Violaxanthin De-epoxidase, Xanthophylls and Ascorbate in Spinach Upon Shift From Low to High Light", Photosynthesis Research, vol. 57, pp. 41-50 (1998).
Gautier et al., "How Does Tomato Quality (Sugar, Acid, and Nutritional Quality) Vary with Ripening Stage, Temperature, and Irradiance?", J. Agric. Food Chem., vol. 56, pp. 1241-1250 (2008).
Gil et al., "Changes in Pomegranate Juice Pigmentaton During Ripening", J. Sci. Food Agric., vol. 68, pp. 77-81 (1995).
Poiroux-Gonord, Health Benefits of Vitamins and Secondary Metabolites of Fruits and Vegetables and Prospects to Increase Their Concentrations by Agronomic Approaches, J. Agric. Food Chem. 58, pp. 12065-12082 (2010).
Heuberger et al., "Precision Stressing by UV-B Radiation to Improve Quality of Spinach Under Protected Cultivation", Acta Hortic., vol. 659, pp. 201-206 (2004).
Jansen et al., "Plant Stress and Human Health: Do Human Consumers Benefit From UV-B Acclimated Crops?" Plant Science, vol. 175, pp. 449-458 (2008).
Ju et al., "Effects of Covering the Orchard Floor With Reflecting Films on Pigment Accumulation and Fruit Coloration in Fuji' Apples", Scientia Horticulturae, vol. 82, pp. 47-56 (1999).
Kim et al., "Quality of Fresh-Cut Tomtoes as Affected by Salt Content in Irrigation Water and Post-Processing Ulraviolet-C Treatment", J. Sci. Food Agric., vol. 88, pp. 1969-1974 (2008).
Kondo et al., "Antioxidant Activity in Meiwa Kumquat as Affected by Environmental and Growing Factors", Environmental and Experimental Botany, vol. 54, pp. 60-68 (2005).
Lee et al., "Preharvest and Postharvest Factors Influencing Vitamin C Content of Horticultural Crops", Postharvest Biology and Technology, vol. 20, pp. 207-220 (2000).
Li et al., "The Shaded Side of Apple Fruit Becomes More Sensitive to PhotoInhibition With Fruit Development", Physiologia Plantarum, vol. 134, pp. 282-292 (2008).
Mancinelli, "Light-Dependent Anthocyanin Synthesis: A Model System for the Study of Plant Photomorphogenesis", The Botanical Review, vol. 51, pp. 107-157 (1985).
Merzlyak et al., "Patterns of Pigment Changes in Apple Fruits During Adaptation to High Sunlight and Sunscald Development", Plant Physical Biochem, vol. 40, pp. 679-684 (2002).
Myung-Min et al., "Environmental Stresses Induce Health-Promoting Phytochemicals in Lettuce", Plant Physiology and Biochemistry, vol. 47, pp. 578-583 (2009).
Naranjo et al., Plastics Testing and Characterization-Industrial Applications, Hanser Gardner Publishers: Cincinnati (2008).
Ravichandiran et al., "Synthesis of Heterocyclic Naphthoquinone Derivatives as Potent Organic Fluorescent Switching Molecules", Journal of Taibah University for Science, vol. 9, pp. 538 (2015).
Rudell et al., "Methyl Jasmonate Enhances Anthocyanin Accumulation and Modifies Production of Phenolics and Pigments in 'Fuji' Apples", J. Amer. Soc. Hort. Sci. vol. 127(3), pp. 435-441 (2002).
Schonhof et al., "Effect of Temperature Increase Under Low Radiation Conditions on Phytochemicals and Ascorbic Acid in Greenhouse Grown Broccoli", Agriculture: Ecosysems and Environment, vol. 119, pp. 103-111 (2007).
Schwanz et al., "Antioxidants in Sun and Shade Leaves of Sour Orange Trees (Citrus Aurantium) After Long-Term Acclimation to Elevated $CO_2$", Journal of Experimental Botany, vol. 47, pp. 1941-1950 (1996).
Torres et al., "Physiological and Biochemical Responses of Fruit Exocarp of Tomato (Lycopersicon Esculentum Mill.) Mutants to Natural Photo-Oxidative Conditions", Journal of Experimental, vol. 57, pp. 1933-1947 (2006).
Ubi et al., "Expression Analysis of Anthocyanin Biosynthetic Genes in Apple Skin: Effect of UV-B and Temperature", Plant Science, vol. 170, pp. 571-578 (2006).
Wilkens et al., "Differential responses of growth and two soluble phenolics of tomato to resource availability." Ecology, vol. 77, pp. 247-258 (1996).
Zhou et al., "Red Light Stimulates Flowering and Anthocyanin Biosynthesis in American Cranberry," Plant Growth Regulation, vol. 38, pp. 165-171 (2002).

* cited by examiner

METHOD FOR OPTIMIZING PLASTIC COMPOSITIONS USED IN PACKAGING TO INCREASE SHELF-LIFE OF PERISHABLE PRODUCTS AND A SYSTEM THEREOF

This application claims the benefit of U.S. Provisional Patent Application Ser. No. 62/324,790, filed Apr. 19, 2016, which is hereby incorporated by reference in its entirety.

FIELD OF THE INVENTION

The present application relates to methods and systems for optimizing plastic compositions formed from resin feedstocks, and more specifically to optimal blending or the use of modifiers/additives in recycled thermoplastic in packaging to increase shelf-life of perishable products.

BACKGROUND OF THE INVENTION

In recent years, federal and state legislation has been proposed to increase the use of sustainable (bio-based) and recycled packaging materials. The adoption of recycled plastic or bio-plastic alternatives has been slow due to contaminant loads, the costs associated with collection and sorting, and overall quality. Bio-plastics have been viewed as a costly alternative to traditional plastics. Thus, there is a need to incentivize the use of bioplastics and recycled packaging materials.

Agricultural growers and packers utilize plastic packaging for retail convenience foods and food service products and are currently the largest users of plastic film and sheeting in the United States. Studies have indicated that the vitamin content of current fruits and vegetables is significantly lower than 50 years ago. This is important as most Americans do not eat enough of these products.

It has been suggested that the increased haze, scattering, and filtering of light in recycled and bio-plastic substrates reduces the rate of product degradation. As such, recent initiatives by retailers have called for an increase in the use of recycled packaging substrates. However, the nature of recycled packaging material, which includes variance in the overall composition, makes it difficult to predict how effective the final plastic product will be at providing these benefits. Further, once the product is finalized, there is no opportunity to adjust the composition to provide the maximum benefit with respect to increasing the shelf-life of perishable products.

The present invention is directed to overcoming these and other deficiencies in the art.

SUMMARY OF THE INVENTION

One aspect of the present invention relates to a method of optimizing a plastic composition formed from a plurality of resin feedstocks. A plurality of resin feedstocks are provided. The plurality of resin feedstocks are blended to form the plastic composition. One or more properties of the plastic composition, including radiation absorption, radiation transmission, gas evolution, fluorescence, or melting properties, are measured. The ratio of the plurality of resin feedstocks being blended into the plastic composition is adjusted, based on the measured one or more properties, to form an optimized plastic composition.

Another aspect of the present invention relates to a system including a blending apparatus configured to blend a plurality of resin feedstocks. One or more sensors are positioned at different locations in the blending apparatus to measure one or more properties of the plurality of resin feedstocks, including radiation absorption, radiation transmission, photoionization, or melting properties. The system further includes a computing device comprising a processor and a memory coupled to the processor which is configured to execute one or more programmed instructions stored in the memory and comprising receiving measurements of the one or more properties of the plurality of resin feedstocks from the one or more sensors and outputting one or more instructions to the blending apparatus to blend the plurality of resin feedstocks based on the measured one or more properties to optimize the plastic composition. A compound delivery system is configured to blend the plurality of resin feedstocks based on the one or more properties.

This technology provides increases in nutritive retention and shelf-life, as well as perceived freshness of vegetables, when utilizing recycled and bio-plastics of varying composition. Many compounds have been identified as contributing to the light filtering effect seen in recycled plastics. The present technology allows for the presence of these compounds to be modified by optimal blending or by using additives s part of the recycling process or during conversion and manufacturing to optimize the resultant plastic composition to provide extended shelf-life for products stored therein.

Utilizing the present technology, various radiation, absorption, emission, fluorescence, and thermal properties of plastic compositions are measured during the conversion of resin feedstocks to a plastic composition. The measured properties provide data that may be utilized to adjust the blending of the resin feedstocks or to add additional materials to the blend to optimize the resultant plastic composition to provide longer shelf-life and reduce degradation for products stored in the plastic composition.

DETAILED DESCRIPTION OF THE INVENTION

The present application relates to methods and devices for optimizing plastic compositions formed from resin feedstocks, and more specifically to the use of modifiers in recycled thermoplastic in packaging to increase shelf-life of perishable products.

One aspect of the present invention relates to a system including a blending apparatus configured to blend a plurality of resin feedstocks. One or more sensors are positioned at different locations in the blending apparatus to measure one or more properties of the plurality of resin feedstocks, including radiation absorption, radiation transmission, photoionization, or melting properties. The system further includes a computing device comprising a processor and a memory coupled to the processor which is configured to execute one or more programmed instructions stored in the memory and comprising receiving measurements of the one or more properties of the plurality of resin feedstocks from the one or more sensors and outputting one or more instructions to the blending apparatus to blend the plurality of resin feedstocks based on the measured one or more properties to optimize the plastic composition. A compound delivery system is configured to blend the plurality of resin feedstocks based on the one or more measured properties.

Figure 1:
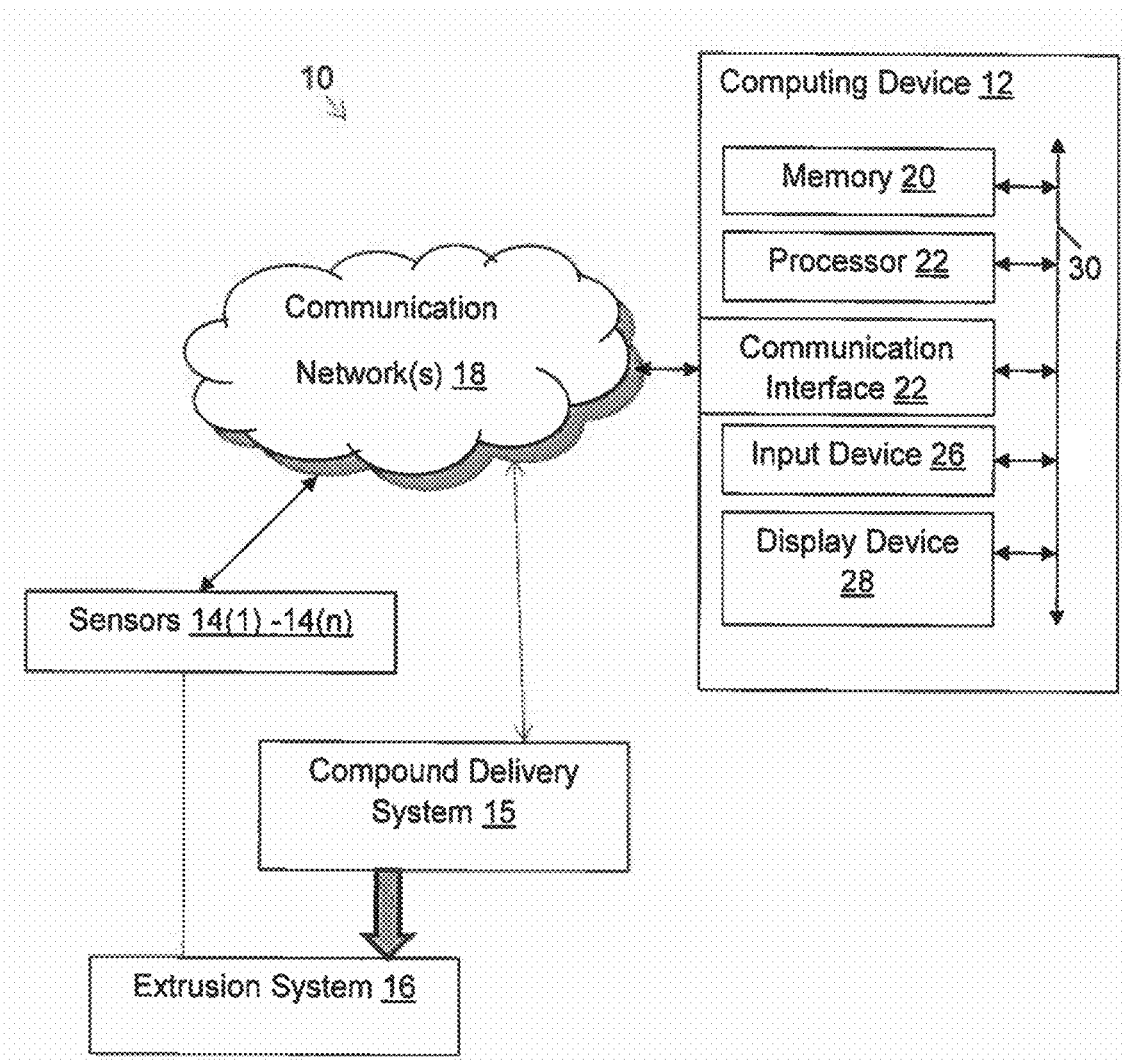
FIG. 1 is an exemplary environment including a computing device coupled to one or more sensors to optimize or increase performance of a plastic composition in accordance with the present technology.

An exemplary environment 10 including a computing device 12 coupled to one or more sensors 14(1)-14(n) and a compound delivery system 15 by a communication network 18 is illustrated in FIG. 1. While not shown, the environment also may include additional components whose connections and operations are well known to those of ordinary skill in the art and thus will not be described here. Sensors 14(1)-14(n) are coupled to a blending apparatus, such as an extrusion system 16, although sensors 14(1)-14(n) may be coupled to other blending apparatuses such as an injection system or a resin conversion system, by way of example. Sensors 14(1)-14(n) are positioned at different locations in extrusion system 16, such as locations 102-109 as illustrated in FIG. 2. This technology provides a number of advantages including a system and methods that more effectively optimize plastic compositions formed from a plurality of resin feedstocks. By way of example, the plastic compositions may be optimized to isolate and control absorption, transmission, or emission of electromagnetic wavelengths to improve the consumer performance of food or beverage containers constructed from the plastic compositions. The food or beverage containers constructed from the optimized plastic compositions advantageously provide for increased shelf-life and reduced product and nutrient decay of items stored therein.

Referring again more specifically to FIG. 1, computing device 12 in this example is configured to be capable of receiving measurements of one or more properties of the plurality of resin feedstocks from sensors 14(1)-14(n) and outputting one or more instructions to compound delivery system 15 or extrusion system 16 to blend the plurality of resin feedstocks based on the measured properties in order to optimize the plastic composition, as illustrated and described with examples of the methods described herein. Computing device 12 includes at least a processor 20, a memory 22, a communication interface 24, an input device 26, and a display device 28, which are coupled together by a bus 30 or other communication link, although other numbers and types of systems, devices, components, and elements in other configurations and locations can be used.

Processor 20 in computing device 12 executes a program of instructions stored in the memory for one or more aspects of the present technology, although other numbers and types of systems, devices, components, and elements in other configurations and locations can be used.

Memory 22 in computing device 12 stores the programmed instructions for one or more aspects of the present technology, although some or all of the programmed instructions could be stored and/or executed elsewhere. A variety of different types of memory storage devices, such as a random access memory (RAM), read only memory (ROM), hard disk, CD ROM, DVD ROM, or other computer readable medium which is read from and written to by a magnetic, optical, or other reading and writing system that is coupled to processor 20, can be used for memory 22.

Communication interface 24 of the computing device 12 is used to operatively couple and communicate between the computing device 12 and sensors 14(1)-14(n) via the communications network 18, although other types and numbers of communication networks, systems, or other links with other types and numbers of connections and configurations can be used. By way of example only, communications network 18 could use TCP/IP over Ethernet and industry-standard protocols, including NFS, CIFS, SOAP, XML, LDAP, and SNMP, although other types and numbers of communication networks, such as a direct connection, a local area network, a wide area network, modems and phone lines, e-mail, and wireless communication technology, each having their own communications protocols, can be used.

Input device 26 and display device 28 of computing device 12 enable a user to interact with computing device 12, such as to input and/or view data and/or to configure, program, and/or operate computing device 12. Input device 26 may include a keyboard, computer mouse, and/or touch screen and display device 28 may include a computer monitor, although other types and numbers of input devices and/or display devices could also be used in other examples. Input device 26, by way of example, may be utilized to manually input data regarding one or more properties of the plastic composition.

Sensors 14(1)-14(n) may be any sensors known in the art capable of measuring one or more properties of a plastic composition in accordance with the examples of methods illustrated and described herein. Although a plurality of sensors 14(1)-14(n) are illustrated, it is to be understood that a single sensor could be utilized in some examples. By way of example, sensors 14(1)-14(n) are configured to measure radiation absorption, radiation transmission, gas evolution, radiation fluorescence, or melting properties of a plastic composition.

Sensors 14(1)-14(n) may be configured to perform, by way of example, ultraviolet-visible spectroscopy analysis, an attenuated total reflectance Fourier transform infrared spectroscopy analysis, a differential scanning calorimetry analysis, a mechanical analysis, x-ray fluorescence analysis, or energy dispersive x-ray fluorescence analysis of the plastic composition. It is to be understood that sensors 14(1)-14(n) are not limited to these measurement techniques, and other analytical techniques may be employed that are suitable for obtaining one or more properties of a plastic composition.

In one example, an ultraviolet visible spectrometer may be utilized. The ultraviolet visible spectrometer must have sufficient resolution to generate a spectrum of absorbance as a function of the wavelength of the incident irradiation between 300 nm and 400 nm. The range of absorption measurement analysis may be lower than 300 nm and higher than 400 nm depending on the desired absorption properties of the product. The thickness of the specimen analyzed (perpendicular to the incident irradiation) is measured as the thickness of the specimen affects the measured absorption properties. A single wavelength absorption measurement may be sufficient if the data represents the desired ultraviolet/visible absorption properties or under rapid throughput conditions for quality control.

In another example, Fourier transform infrared spectroscopy is utilized. A background spectrum is collected and stored. The minimum number of scans collected for the background spectrum will be considered as the number of scans that generates a representative spectrum of the background environment. The collected spectra may be normalized (i.e., the spectrum is multiplied by a number) to the intensity of a wavenumber that is representative of a characteristic band of the polymer that does not change in intensity due to a chemical reaction. In addition, transmission experiments may be normalized by the path length of the specimen (typically the thickness of the specimen). In certain cases, a mathematical subtraction may be performed to emphasize spectral shifts according to equation 1.

$$A(v)_{subtracted\ spectrum} = A(v)_{spectrum\ A} - A(v)_{spectrum\ B} \quad [1]$$

In yet another example, fluorescence intensity measurements are made with an instrument capable of irradiating the sample with ultraviolet and visible light and detecting the fluorescence response. The instrument must at minimum be able to irradiate the sample at 350 nm excitation wavelength, however, other excitation wavelengths may be used for analysis. The fluorescence detector must at minimum be able to detect the intensity of the fluorescence emission at 501 nm, however, the fluorescence intensity of other emission wavelengths may be used for analysis so long as the data are indicative of the properties indicated in this invention. In some cases, a "3D" scan can be employed where the fluorescence intensity of at a given wavelength for a specific excitation wavelength for multiple sequential excitation wavelengths at a known interval.

Figure 2A:
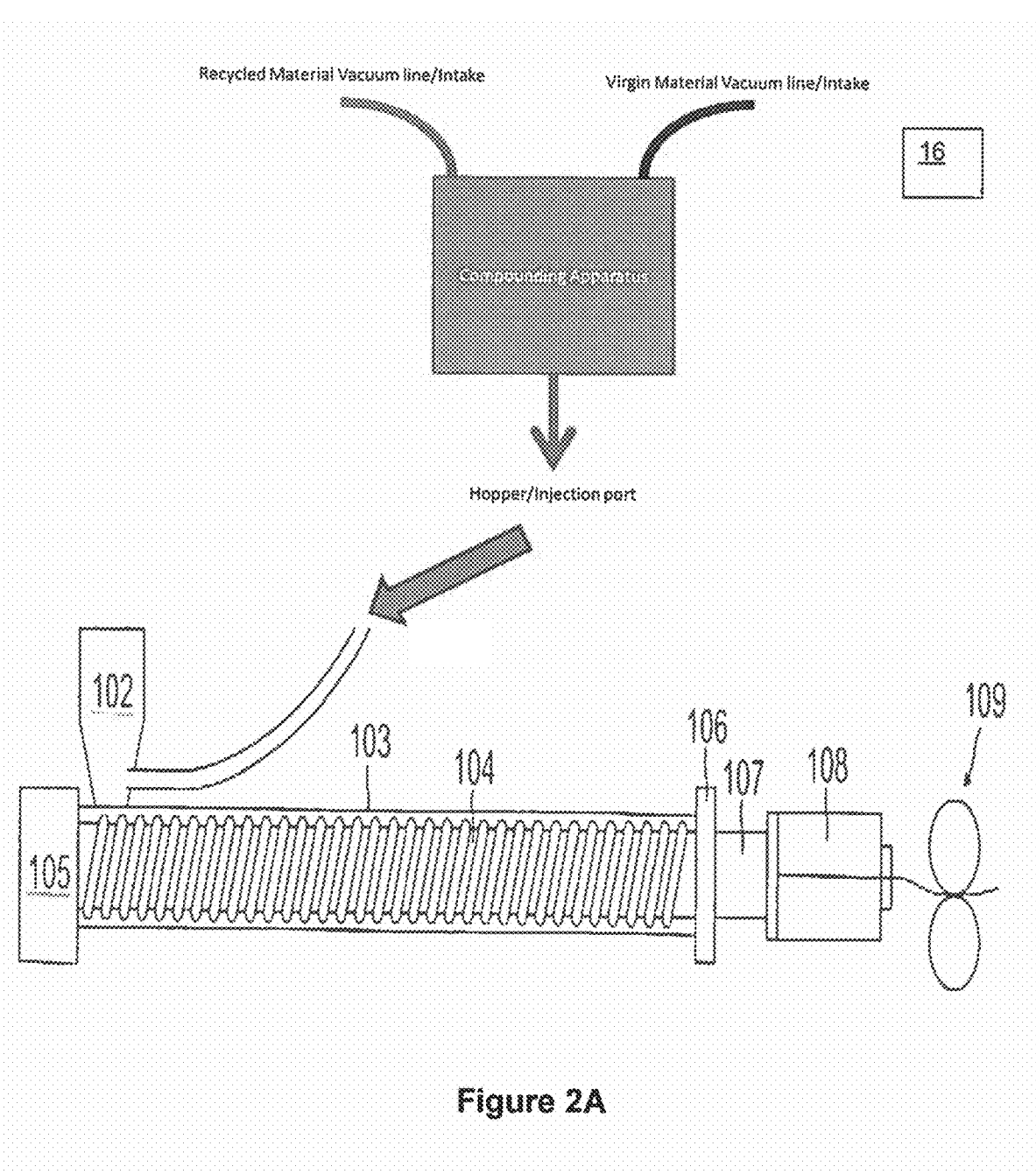
FIG. 2A shows a side view of an exemplary extrusion system.

Sensors 14(1)-14(n) are located at positions 102-109 in extrusion system 16 as illustrated in FIG. 2A to measure the properties of the plastic composition at various points in the extrusion process. In one example, the measuring is carried out at a single point in time following blending of the plurality of resin feedstocks to form the plastic composition. In another example, the measuring is carried out at least two different points in time following blending of the plurality of resin feedstocks to form the plastic composition. More specifically, by way of example only, a UV-Vis measurement and X-ray fluorescence elemental analysis may be performed on the extruded sheet between the first and second rollers on the take up apparatus as illustrated in FIG. 2. Sensors 14(1)-14(n) communicate the measured properties of the plastic composition to computing device 12 via communication network 18.

Figure 2B:
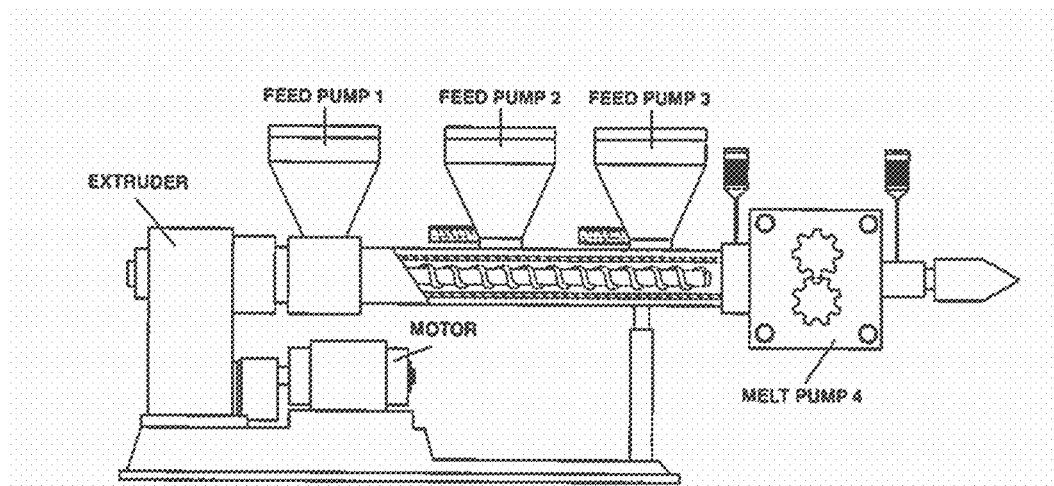
FIG. 2B shows a side view of another exemplary extrusion system.

Compound delivery system 15 is coupled to extrusion system 16 and is configured to blend the plurality of resin feedstocks in the extrusion system 15 based on the one or more properties of the plastic composition measured by sensors 14(1)-14(n) as illustrated in FIG. 2A. By way of example, compound delivery system 15 is one or more of a co-extruder, a dosing pump, or a direct intake to an extrusion line of extrusion system 16. In another example, as illustrated in FIG. 2B, a plurality of feed pumps 1-3 may be utilized. In one example, compound delivery system 15 adjusts the ratio of the feedstock resins in extrusion system 16. In another example, compound delivery system 15 is configured to add one or more additive compounds to the plastic composition during the extrusion process. Compound delivery system 15 is manually controlled to adjust the blending of the plurality of feedstock resins. Alternatively, compound delivery system 15 is part of an automatic feedback loop with the adjusting of the blending of the plurality feedstock resins controlled by computing device 12, as described herein.

Although an example of environment 10 including computing device 12 is described herein, it is to be understood that the devices and systems of the examples described herein are for exemplary purposes, as many variations of the specific hardware and software used to implement the examples are possible, as will be appreciated by those skilled in the relevant art(s).

Aspects of the examples may also be embodied as a non-transitory computer readable medium having instructions stored thereon for one or more aspects of the present technology as described and illustrated by way of the examples herein, as described herein, which when executed by a processor, cause the processor to carry out the steps necessary to implement the methods of the examples, as described and illustrated herein.

Another aspect of the present invention relates to a method of optimizing a plastic composition formed from a plurality of resin feedstocks. A plurality of resin feedstocks are provided. The plurality of resin feedstocks are blended to form the plastic composition. One or more properties of the plastic composition, including radiation absorption, radiation transmission, gas evolution, radiation fluorescence, or melting properties, are measured. The ratio of the plurality of resin feedstocks being blended into the plastic composition is adjusted, based on the measured one or more properties, to form an optimized plastic composition.

Figure 3:
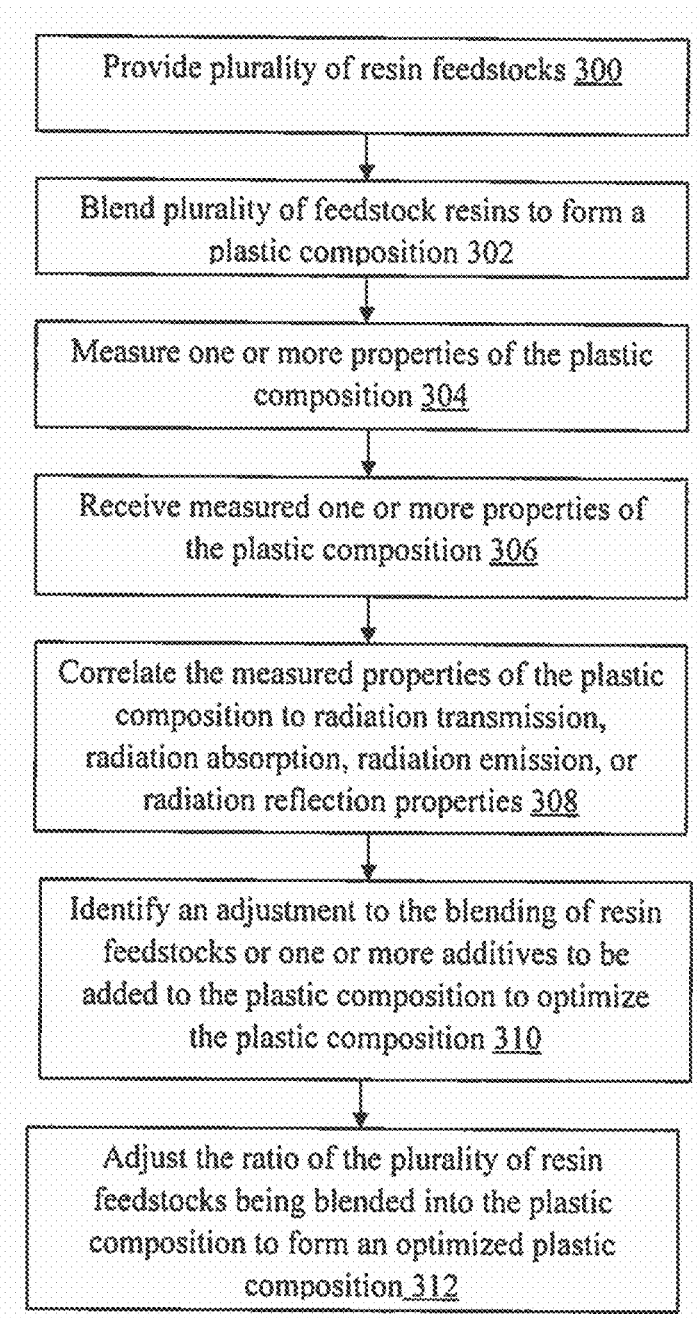
FIG. 3 is a flow chart of an exemplary method for optimizing a plastic composition made from feedstock resins.

An exemplary method for optimizing a plastic composition in accordance with the present technology will now be described with respect of FIGS. 1-3.

In step 300, a plurality of resin feedstocks are provided. In one example, the resin feedstocks are thermoplastic resin feedstocks, such as polyethylene terephthalate (PET), although other thermoplastic resin feedstocks such as polyethylene, polypropylene, polystyrene, poly methyl methacrylate, polycarbonate, an addition polymer, a condensation polymer, and mixtures thereof, may be utilized. The plurality of resin feedstocks may include a recycled polymeric material and a virgin polymeric material, although in one example only recycled polymeric material is utilized. The plurality of resin feedstocks may be provided in various combinations depending upon the application.

Next, in step 302, the plurality of resin feedstocks are blended to form the plastic composition. The plurality of resin feedstocks are blended in a blending apparatus, such as extrusion system 16 illustrated in FIG. 2, although other blending apparatuses such as an injection system or a resin conversion systems, by way of example, may be utilized. Methods of blending resin feedstocks to form a plastic composition are well known in the art and will not be described herein.

In step 304, one or more properties of the plastic composition are measured by sensors 14(1)-14(n) coupled to extrusion system 16. Although a plurality of sensors 14(1)-14(n) are illustrated, it is to be understood that a single sensor could be utilized at single measurement location. The one or more measured properties of the plastic composition include one or more of radiation absorption, radiation transmission, gas evolution, radiation fluorescence, or melting properties. In one example, the measuring in step 304 is carried out at least two different points in time following the blending in step 302. The measuring in step 304 may be performed using ultraviolet-visible spectroscopy analysis, an attenuated total reflectance Fourier transform infrared spectroscopy analysis, a differential scanning calorimetry analysis, a mechanical analysis, x-ray fluorescence analysis, or energy dispersive x-ray fluorescence analysis. It is to be understood that the measuring performed is not limited to these measurement techniques, and other analytical techniques may be employed that are suitable for obtaining one or more properties of a plastic composition. In one example, the measuring is performed by sensors 14(1)-14(n), which may be located at various locations along extrusion system 16, such as locations 102-109 illustrated in FIG. 2.

Next, in step 306, computing device 12 receives the measured properties from sensors 14(1)-14(n) through communication network 18. Alternatively, the one or more properties may be measured by sensors 14(1)-14(n) and entered manually into computing device 12 through input device 26. Computing device 12 may receive data from sensors 14(1)-14(n) at multiple points in time during the conversion process.

In step 308, computing device 12 correlates the measured properties of the plastic composition to radiation transmission, radiation absorption, radiation emission, or radiation reflection properties for a completed plastic composition product having those measurements.

In step 310, computing device 12 identifies an adjustment to the blending of resin feedstocks or one or more additives to be added to the plastic composition to optimize these properties. More specifically, if the absorption properties desired are more similar to the absorption properties of a composition comprising 75% RPET and the measured absorption properties are more closely associated with 25% RPET, then the computing device 12 can alter the feed ratio of the resin feedstocks utilizing a calibrated single wavelength measurement (e.g., 350 nm) to adjust the composition ratio to achieve the desired absorption spectrum as described in FIG. 4A and FIG. 10. The general steps for identifying an adjustment to the blending of resin feedstocks or one or more additives to be added is as follows: 1) utilize previously described sensor data, such as spectral analysis, to determine a set of potential indicators; 2) identify a set of indicators that are independent of contamination by sensors such as spectral analysis and other ionization sensors; 3) use the set of indicators to determine samples with and without contamination loads and isolate indicators to sensor analysis such as spectral characteristics; 4) utilize a series of algorithms for each level of recycled content to interpret sensor signals and assign contribution value of each indicator as a function of wavelength isolation, filtering capacity, and shelf-life extension through isolation and blocking of known vitamin degradation wavelengths In step 312, the ratio of the plurality of resin feedstocks being blended into the plastic composition is adjusted, based on said measuring, to form an optimized plastic composition. The plastic composition is optimized based on radiation transmission, radiation absorption, radiation emission, or radiation reflection properties. The radiation transmission, radiation absorption, radiation emission, or radiation reflection properties are optimized so the optimized plastic composition isolates and controls electromagnetic wavelengths associated with one or more of vitamin degradation, adverse color changes, chlorophyll degradation, or degradation of other nutritional components. In one example, the plastic composition blocks between 50% to 75% more of incident ultraviolet light compared to the plastic composition not containing recycled content at an exemplary thickness of 20 microns. The optimized properties allow for increased shelf-life of products stored in the plastic composition. By way of example, the blending of the plastic composition is optimized to isolate certain destructive wavelengths for particular vitamins/compounds as illustrated in Table 1 below, which identifies wavelengths associated with nutrient degradation loss for the listed nutrients.

Table 1 below, which identifies wavelengths associated with nutrient degradation loss for the listed nutrients.

TABLE 1

Wavelengths associated with nutrient degradation/loss for a given nutrient

| Vitamin/Compound | UV (nm)/ Visible (nm) | Protective Compound |
| --- | --- | --- |
| Vitamin A | 330-350 | |
| Vitamin C (ascorbic acid) | 265 | |
| Chlorophyll | 280-400 429, 659 | |
| Chlorophyll b | 280-400 455, 642 | |
| Carotenoids (B-carotene, lutein, xanthophyll) | 280-400 | 400-500 |
| Anthocyanins | 278-313 517 | |
| Riboflavin (vitamin B2) | 200-400 400-500 | 200-33 |
| Myoglobin | 200-300 570-590 | 200-300 |
| Tocopherol (vitamin E) | 292 | |

In one example, the blending is carried out using compound delivery system 15, such as a co-extruder, a dosing pump, or a direct intake to an extrusion line. Compound delivery system 15 may be located at any one of the locations 102-109 in extrusion system 16 as illustrated in FIG. 2. In one example, compound delivery system 15 is manually controlled to adjust the blending of the plurality of feedstock resins based on an output on display device 28 of computing device 12. Alternatively, compound delivery system 15 is part of an automatic feedback loop such that the adjusting of the blending of the plurality feedstock resins is directly controlled by computing device 12. In one example, compound delivery system 15 adjusts the ratio of the feedstock resins in extrusion system 16. In another example, compound delivery system 15 is configured to add one or more additive compounds to the plastic composition during the extrusion process.

One or more additive compounds selected from the group consisting of thermal or light stabilizers, antioxidants, plasticizers, fillers, nucleating agents, colorants, thermal conductors, catalysts, and combinations thereof, are added to the plastic composition to provide the optimization in step 312. The one or more additives may be added using compound delivery system 15. Additive compounds are selected, by way of example, to increase light filtering to extend shelf-life. Utilizing this process allows manufacturers to control specifications and monitor the direct or indirect addition of organic and inorganic compounds to feedstock to allow for maximum shelf-life extension, while maintaining customer performance.

Example 1

Data Collection Using Ultraviolet Visible Spectroscopy

Figure 4A:
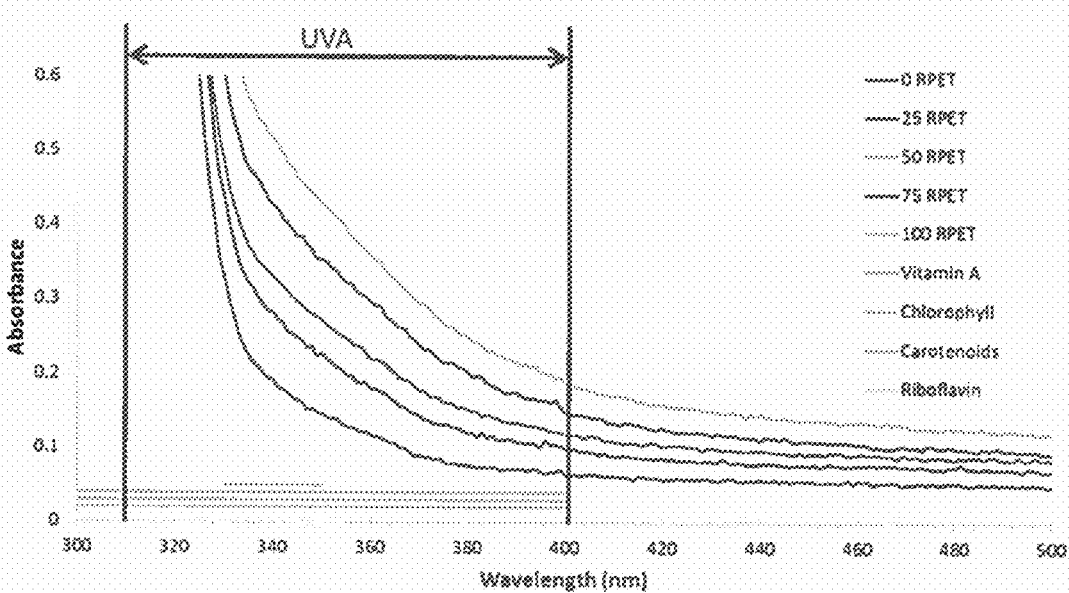
FIGS. 4A and 4B illustrate a UV-Vis spectra (FIG. 4A) and subtraction spectra (x % RPET–0% RPET) (FIG. 4B) of polyethylene terephthalate sheet comprising a varying amount of post-consumer recycled content possessing increased UV radiation absorption. Example nutrients and their respective degradation wavelengths are included for comparison.
Figure 4B:
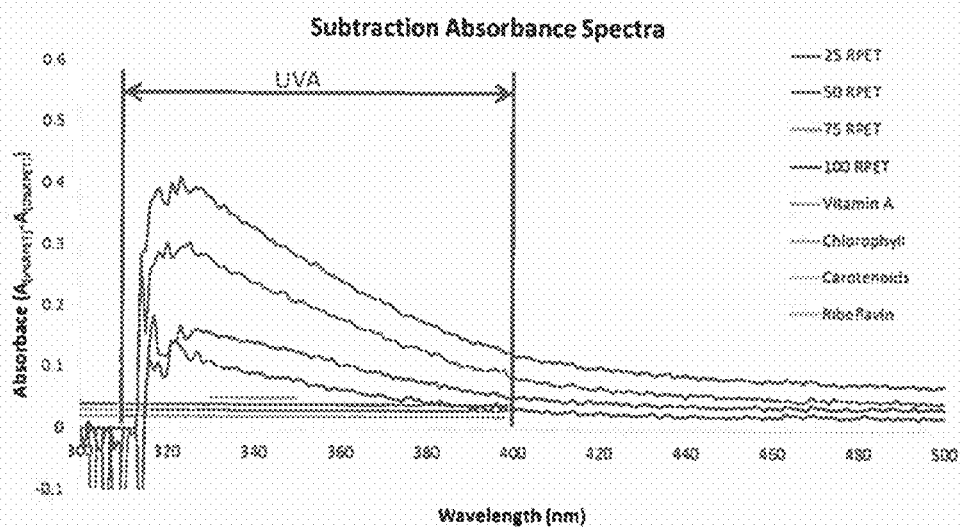

Ultraviolet radiation is broken down into three specific wavelength sections: UVA, UVB, and UVC. Generally, UVC (100-280 nm) is completely absorbed by the atmosphere and UVB (280-315 nm) has a low depth of penetration due to their short wavelengths and therefore typically only result in surface interactions. However, the wavelengths associated with UVA radiation (315-400 nm) are long enough to penetrate tissue and possess sufficient energy to yield detrimental degradation. UV-Vis spectra of the PET sheet absorbed more than the limits of the equipment between 280 and 315 nm independent of RPET concentration, and thus, are expected to perform similarly for absorption of UVB radiation. However, the absorbance of UVA radiation absorption increased with % RPET concentration (FIG. 4A). The increased absorption of these wavelengths would provide protection against UV degradation of nutrients. The area underneath the curve of the subtraction spectra (FIG. 4b) is likely to be related to the quantitative increase of UVA absorption and could possibly be used for incorporation into an empirical model.

Figure 5:
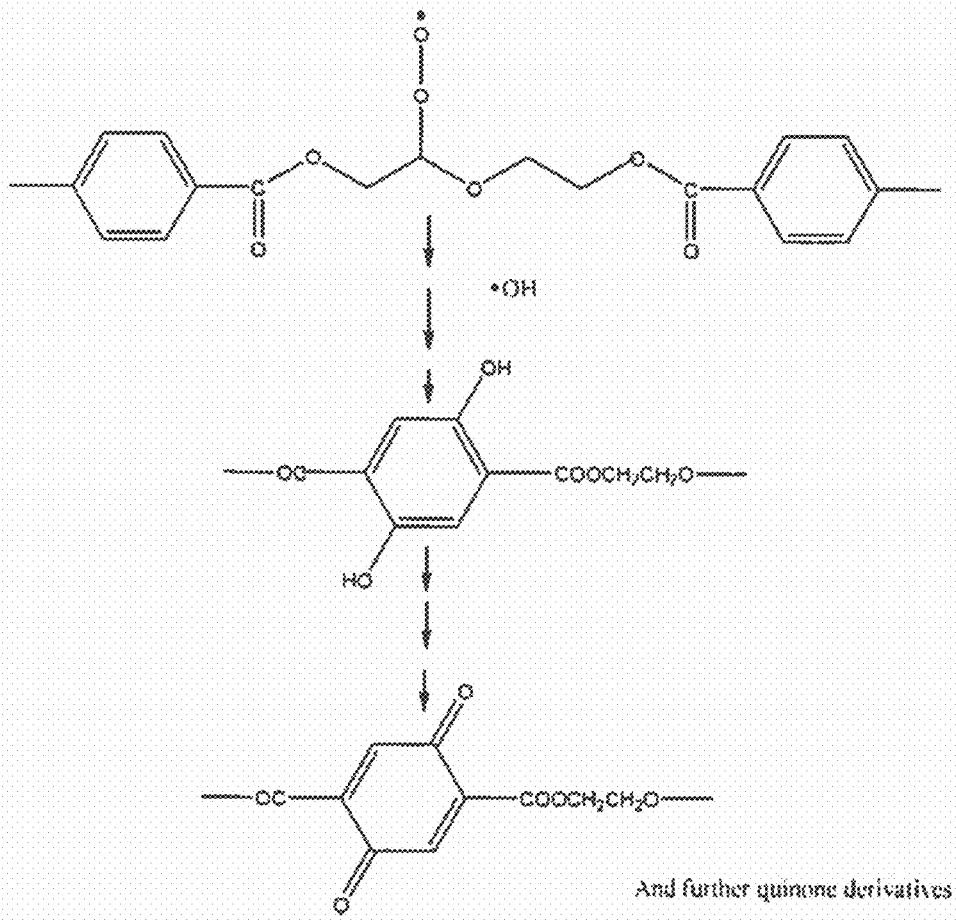
FIG. 5 illustrates a reaction pathway of diethylene glycol constituent under thermos-oxidative conditions of poly(ethylene terephthalate) and subsequent hydroxyl radical reaction with terephthalic acid constituents producing quinone derivatives.
Figure 6:
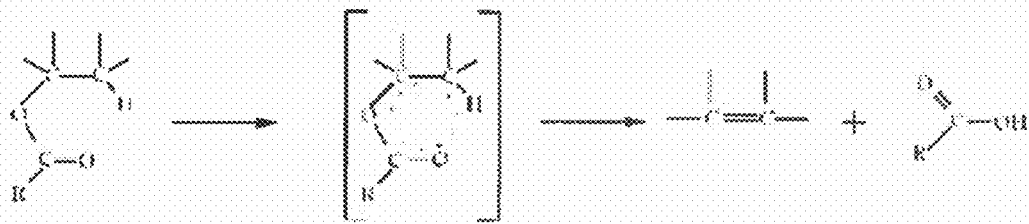
FIG. 6 illustrates a β-scission reaction of poly(ethylene terephthalate) under thermo-oxidative conditions producing alkene and aldehyde functional groups.

Thermo-mechanical processing of polyethylene terephthalate is known to cause main chain degradation of the polymer producing a multitude of degradation byproducts. Thermo-oxidation of PET commonly occurs at the diethylene glycol constituent forming a peroxide compound. The resulting hydroxyl radical reacts with the benzene ring of the terephthalic acid constituent producing quinone/hydroquinone derivatives which are known to absorb UV irradiation (FIG. 5). Additionally, another degradation reaction can produce alkene and aldehyde functional groups via β-scission of the carbon-oxygen bond adjacent to a carbonyl group (FIG. 6). Both alkene and aldehyde functional groups absorb UV radiation. As both degradation mechanisms produce UV absorbing species, blending post-consumer PET with virgin material will result in increased UV absorption.

Figure 7A:
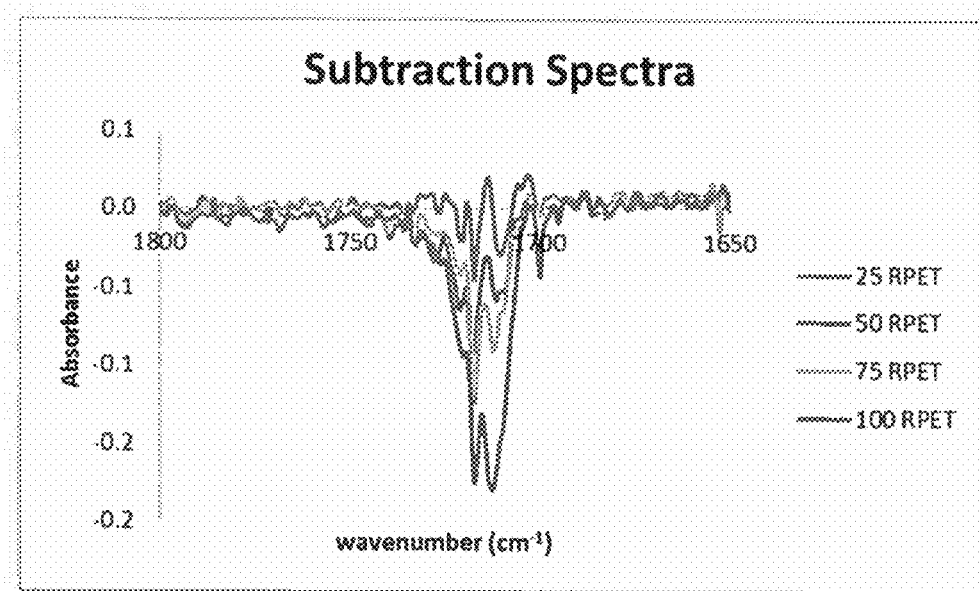
FIGS. 7A and 7B illustrate subtraction attenuated total reflectance Fourier transform infrared spectra of poly(ethylene terephthalate) containing post-consumer recycled content of the carbonyl region (FIG. 7A) and the aromatic ring torsion region (FIG. 7B).
Figure 7B:
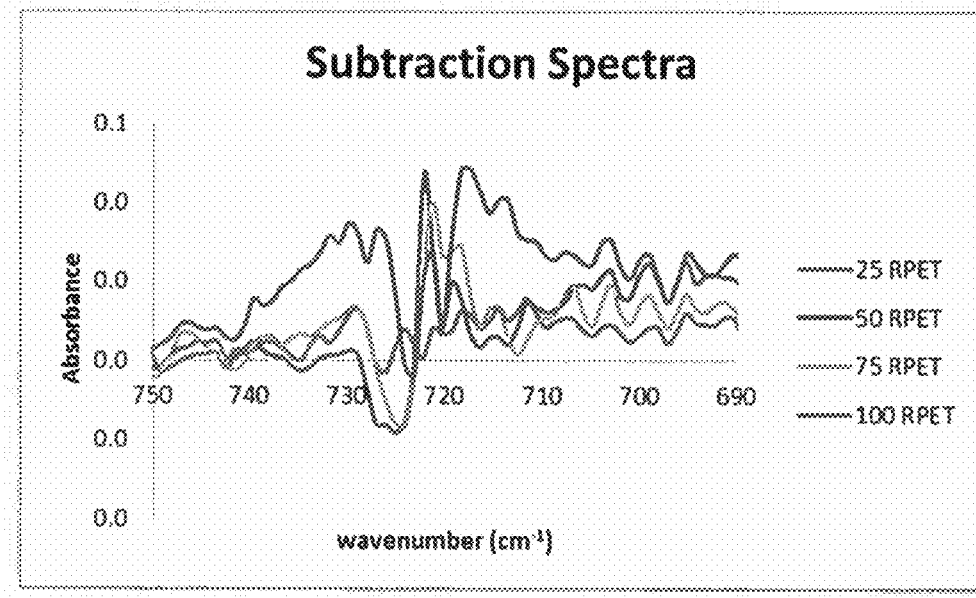

The loss of carbonyl groups detected by attenuated total reflectance Fourier transform infrared spectroscopy increased as a function of increasing recycled content (FIG. 7A). This is attributed to the loss of acetaldehyde, a degradation byproduct, which is known to occur. Additionally, a broadening of the aromatic ring torsion band was observed and is attributed to the reaction of the hydroxyl radical with the terephthalate constituent as discussed above (FIG. 7B).

Figure 8A:
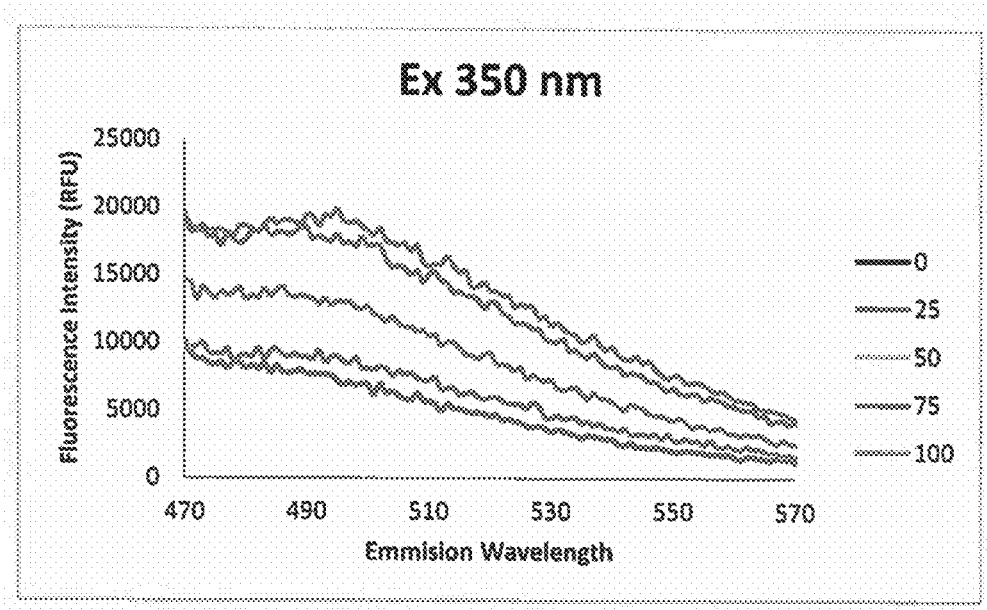
FIGS. 8A and 8B illustrate fluorescence emission spectra of polyethylene terephthalate sheets as a function of percent post-consumer content (FIG. 8A) and the correlation of absorbance at 350 nm with the fluorescence intensity at 501 nm (ex 350) (FIG. 8B).
Figure 8B:
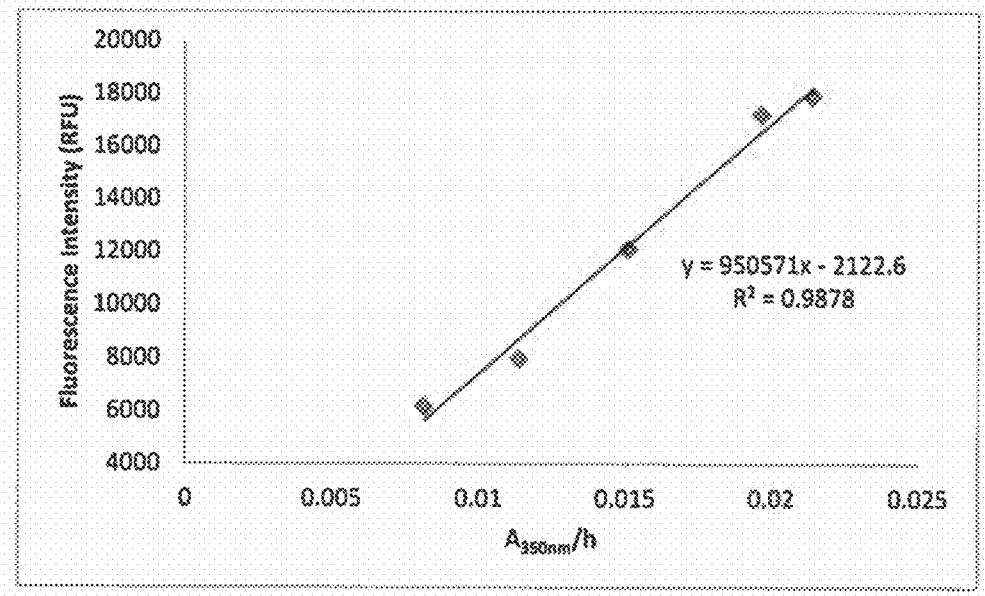

As discussed above, degradation of PET occurs as a result of thermomechanical processing. The mechanisms of degradation in the literature propose the production of quinone derivatives on the aromatic ring of the terephthalic acid constituent which are known to fluoresce. The increased fluorescence intensity between 470 and 570 nm is a result of increased concentration of the fluorescing moiety, which would be produced as a result of degradation events (FIG. 8A). This trend is expected as increasing the PCR content of the sample would increase the mass percent of PET that has undergone degradation events due to additional melt processing cycles. A strong coefficient of determination was observed between the absorbance at 350 nm determined via UV-Vis spectroscopy at the fluorescence intensity at 501 nm (e.g., 350 nm) suggesting that the moiety causing the increased absorbance at 350 nm is due to the quinone derivatives formed during degradation processes (FIG. 8B).

Preliminary Studies for Evaluation of Packaging and Shelf-Life Extension

Figure 11:
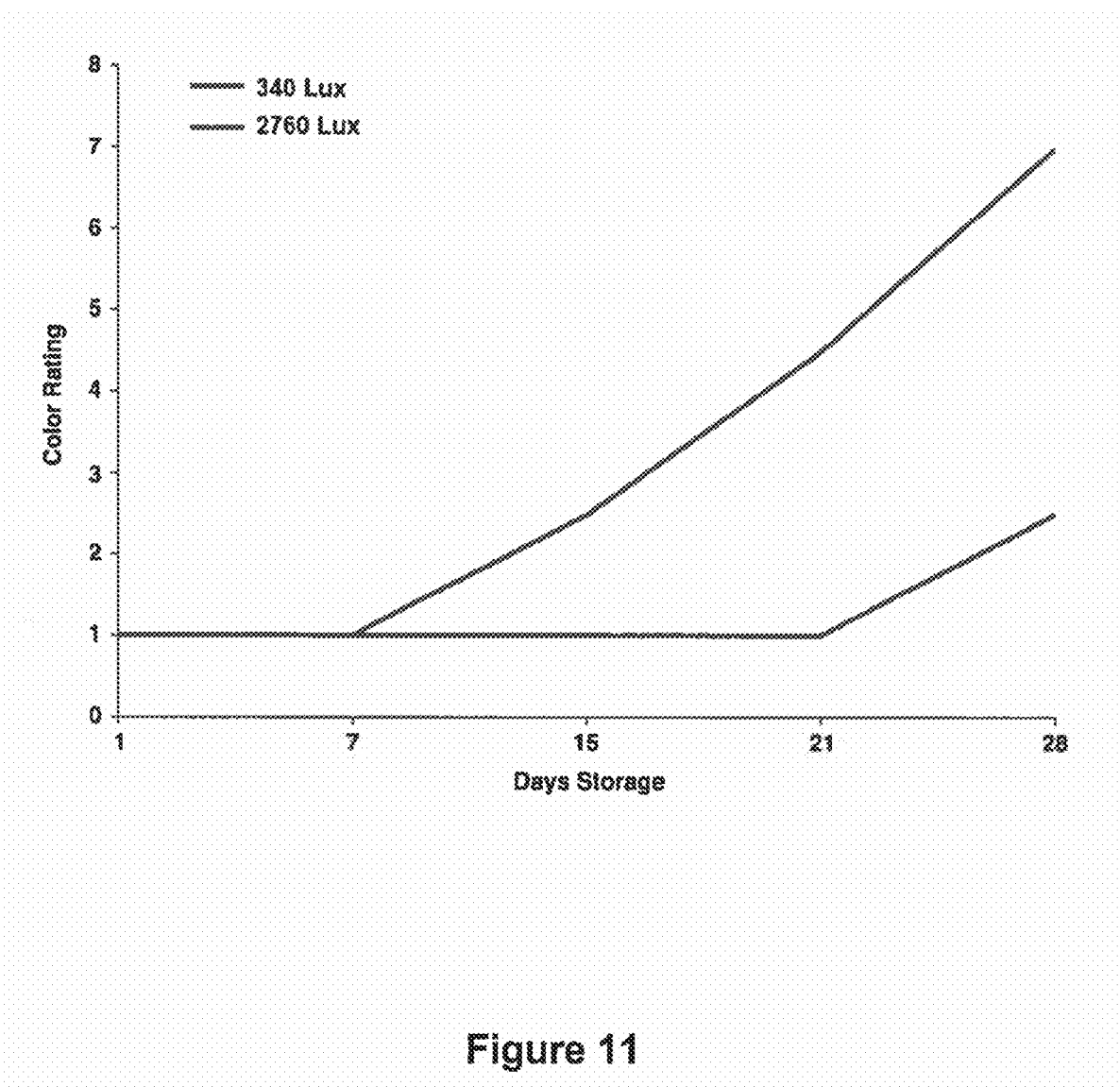
FIG. 11 is graph illustrating color rating vs. days of storage.

Previous work indicated that green vegetables when packaged in recycled content PET containers and exposed to fluorescent light at 276 lux, yellowed and senesced at much faster rates than when stored under dim conditions at 36 lux (FIG. 9) and could be replicated using filtering mechanisms in recycled plastics (FIG. 11).

Freshly-harvested chives (*Allium schoenoprasum* L.) were obtained from a commercial grower in San Diego, Calif. Prior to shipment, the herbs were placed into polyethylene bags with perforations, then immediately cooled by forced air to approximately 4° C. The chives were placed in expanded polystyrene-lined cardboard boxes with pre-cooled gel bags, and shipped via overnight mail. Upon arrival, the herbs were held at 1±0.5 C, and 90% RH. The herbs were used within twenty-four hours.

The chives were placed into non-vented, 907 ml produce containers which were subsequently covered with shrink-wrap film with moderate barrier properties. Each packaging treatment was replicated 4 times with 3 samples per replicate. A weight of 60±2 g of chives was placed into each container and sealed. Packages were placed into a constantly illuminated (fluorescence) controlled environment room held at 1±0.5 C. 90% RH. Samples were randomly placed within the chamber. Average light intensity varied from 2760 lux at the top shelves to 750 lux at the middle shelves, to 340 lux at the bottom shelves of the chambers.

Weights for packages were recorded at the time they were placed into storage. At one-week intervals, two randomly-chosen samples from each treatment were removed and weighed. Samples were compared with fresh, loose samples shipped from the supplier. Variables were rated hedonically on a scale of 1-9, with 1 representing best quality and 9, complete breakdown and tissue destruction. Each package was evaluated for odor, color, wilt, and decay. Values were combined and averaged to produce an overall quality rating. However, when the value for any one variable exceeded 5, the product was considered to be no longer marketable.

Samples containing known amounts of recycled content can extend shelf-life up to 14 days (340 Lux vs 2760 Lux) utilizing filtering mechanisms and through recycled content formulation (FIG. 11).

Manufacture and Characterization of Recycled PET

Manufacture and Testing of Post-Consumer Recycled Sheet:

Recycled PET (RPET) of varying compositions and compounds were dried/recrystallized (<0.2%) using a Farragtech Card E series dryer/crystallizer (Farrag Tech GmbH; Wolfurt, Austria) and blended at approximately 0, 20, 40, 60, 80, and 100% virgin-to-recycled content with varying compound loads as illustrated in Table 2 below. Each converted sheet using RPET blends with compositions of 0, 20, 40, 60, 80, and 100% of virgin/recycled resin was extruded on a single-screw extruder (Davis-Standard, Pawcatuck, Conn.) to a final thickness of 17-20 mil. Sheets were then formed into lidded punnets using a straight vacuum Formech Midi former (Formech Machine; Chicago, Ill.). The thickness of each specimen was recorded at 12 random locations using a digital micrometer with a resolution of ±0.5 µm.

TABLE 2

Example compounds and loading affecting product quality and freshness.

| Additive | Amount |
| --- | --- |
| PVC | <500 ppm |
| Color additive (black, TiOx) | <1000 ppm |
| Barrier Material (PETG) | <6500 ppm |
| Antimony | <500 ppm |
| Acetaldehyde | By blend |
| Boron | <1000 ppm |
| Nucleating agents | <20% crystalline |
| Polymers that phase separate | Depends on size of phase |
| Light stabilizers | WI > 35 |
| Antioxidants | Master batch by blend |
| Residual acids from adhesives | <0.5 g/in2 |

Figure 9:
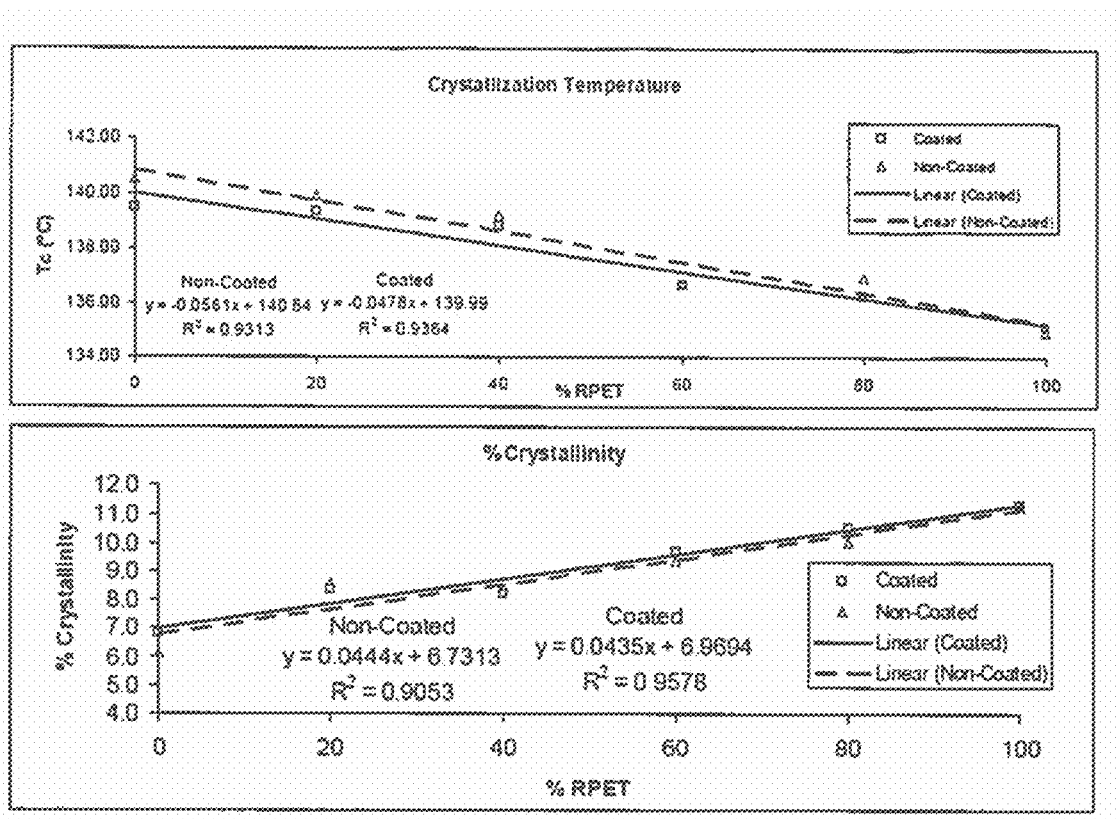
FIG. 9 illustrates example changes in thermal properties of PET due to incorporation of post-consumer recycled content.

Determination of Thermal Properties of Manufactured Sheet:

Differential scanning calorimetry was used to determine the thermal properties of the molded sheets (FIG. 9). Samples (3-6 mg) of each PET/RPET sheet were added to an aluminum pan and hermetically sealed. Each study consisted of heat/cool/heat cycles between 30 and 310° C. at a rate of 10° C./min in accordance with ASTM D3418-03. The crystallization peak onset (Tc onset), crystallization temperature (Tc), crystallization peak offset (Tc offset), crystallization peak width (Tc width), heat of crystallization (ΔHc), percent crystallinity, melting temperature for the first heat cycle (Tm'), heat of melting for the first heat cycle (ΔHm'), glass transition temperature of the cooling cycle (Tg cool), glass transition temperature (Tg), onset of the melting peak for the second heat cycle (Tm" onset), melting temperature of the second heat cycle (T"m), offset of the melting peak for the second heat cycle (Tm" offest), melting peak width of the second heat cycle (Tm" width), and heat of melting for the second heat cycle (ΔHm") were determined using a TA Instruments calorimeter model DSC Q2000 (TA Instruments, DE, U.S.). The first scan was utilized to obtain the Tc onset, Tc, Tc offset, Tc width, ΔHc, % crystallinity, Tm', and ΔHm'. The second scan was used to obtain the Tm" onset, Tm", Tm" offset, Tm" width, and ΔHm".

Figure 10:
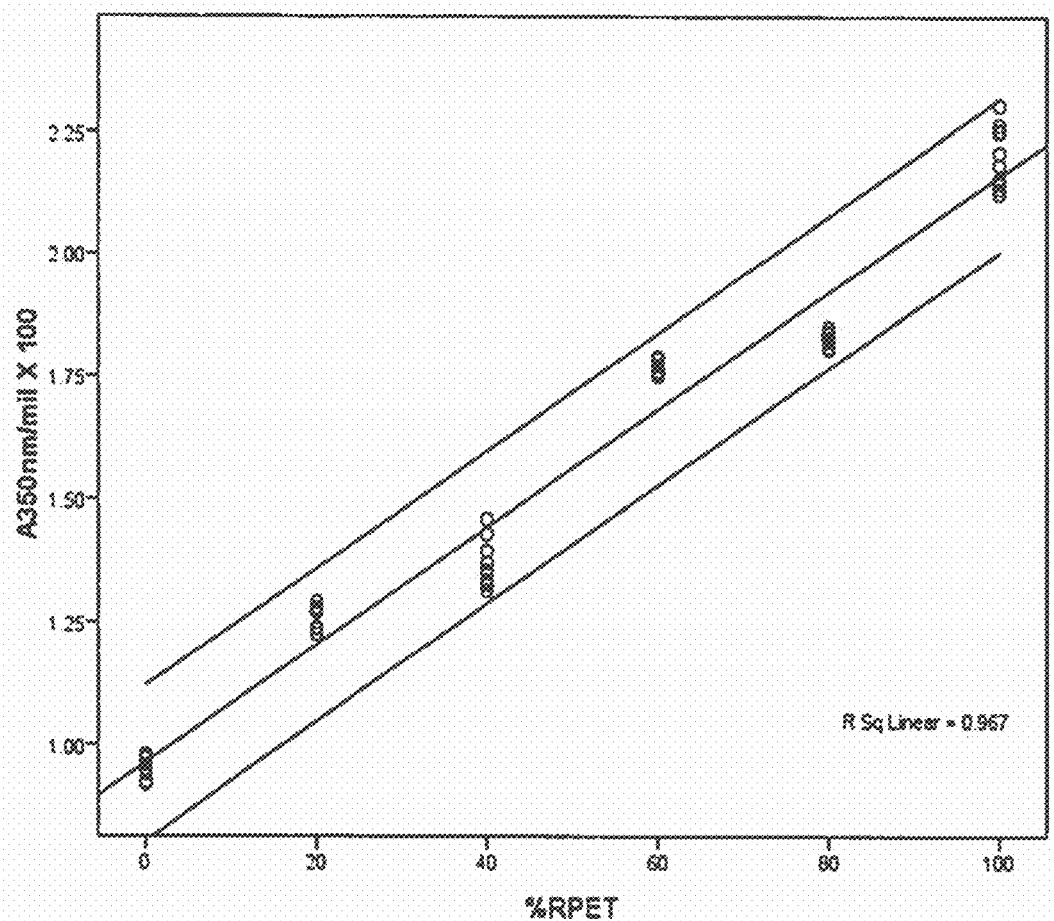
FIG. 10 illustrates changes in ultraviolet visible spectrum absorption of PET due to incorporation of post-consumer recycled content.

Determination of Light Absorption Properties of Manufactured Sheet:

Ultraviolet-visible (UV-Vis) spectroscopy was used to determine the absorption properties of each PET/RPET sheet in the UV-Vis regions (FIG. 10). Each sheet type was scanned between 200-700 nm using a Shimadzu Pharmaspec UV-Vis Spectrometer (model UV-1700, Columbia, Md., U.S.) set to single scan mode at medium speed and sampling intervals of 1.0 nm. The haze (cloudiness) characteristics of the containers as a function of recycled content versus virgin and composition was determined using a commercial haze-gloss hazemeter (Altana, Wesel, Germany). Values were compared to typical haze values for packaged products using RPET and PLA at ≤10% per ASTM D1003 (ASTM, 2000)

Food Packaging and Food Contact Compliance

Chemical Migration of Recycled Polyethylene Terephthalate (RPET):

Domestically manufactured, thermoformed polyethylene terephthalate (PET) containers with label claims of 0, 50, 70, or 100% post-consumer (PC) recycled water bottle content were collected from retail stores. The food simulants specified by 21CFR177.1630 that were used in this study were n-heptane, 8% ethanol in water (v/v), and water. N-heptane (99% Optima grade, Fisher Scientific, Fair Lawn, N.J.) was used as received from the manufacturer. Deionized water (16.7 mega-ohm) was produced using a Barnstead Nanopure II (Dubuque, Iowa) water purification system. A 95% ethanol solution (ACS Spectrophotometric grade, Acros Chemicals, Morris Plains, N.J.) was diluted to 8% (v/v) with nanopure deionized water.

Preparation of Samples:

The experimental design was a completely randomized 3×3 factorial. A circular disk was cut from each package, slightly larger than the area of exposure to ensure a good seal between the sample and the analysis apparatus: the area of exposure to the food simulants was 42.65 $cm^2$ for each sample. Samples were conditioned according to ASTM D618-13 (ASTM 2013) using a Thermo-Forma Scientific environmental chamber coupled to Watlow (Winona, Minn.) 982 series controllers. The mass of each disk was determined using a Mettler Toledo (Columbus, Ohio) Model AB104 scale with a resolution of +/−0.1 mg.

Compounds Contributing to Increased Nutritive Value Retention

Chemical Migration Analyses:

Samples were analyzed for chemical migration according to Title 21, Chapter 1, Subchapter B, Part 177.1630 of the Code of Federal Regulations (CFR 2014). This code requires that each package must not desorb more than 0.5 mg of total chemicals per square inch (6.45 $cm^2$) into specified food simulants: nanopure deionized water, 8% ethanol solution in nanopure deionized water, and n-heptane.

Gas Chromatography—Mass Spectroscopy:

After exposure to the test samples, aliquots of the solvents were injected into a Clarus 600 GC (Perkin Elmer, Shelton, Conn.) equipped with a 0.25 mm I.D., 30 m RTX 502.2 capillary column (Restek, Bellefonte, Pa.) attached to a Perkin Elmer Clarus 600C mass spectrometer (MS). The helium carrier gas was set to a constant flow rate of 2.5 mL/min with the inlet port set to 280° C. The following oven temperature ramping protocol was used: initial temperature 35° C. for 5 min, then increased to 150° C. at a rate of 30° C./min, then increased to 250° C. at a rate of 20° C./min. The final temperature of 250° C. was held for 10 min. Continuous mode MS at a rate of 5 scans/s between m/z ratios of 35 and 300 was employed. Aliquots of pure solvent were analyzed by GC-MS to produce background spectra, the peaks of which were eliminated from the spectra obtained from the food simulants in the 21CFR177.1630 analysis.

Elemental Analysis by Inductively Coupled Plasma-Atomic Emission Spectroscopy:

The PET/RPET sheets were analyzed by inductively coupled plasma-atomic emission spectroscopy (ICP-AES) for elemental composition. California Health and Safety Code 25214.13 states that lead, mercury, cadmium, and hexavalent chromium are contaminants of particular concern and are considered to be regulated metals. One specimen of each sheet was analyzed for elemental composition to confirm that introducing recycled-PET into extruded sheets for food and cosmetic packaging applications meets the requirements of the Toxics in Packaging Prevention Act (California Health and Safety Code 25214.13).

Compound Loading for Increased Freshness

Example compliment additives associated with recycled plastic and biopolymer materials can be found below in ranges that provide optimal light, color and optical properties to increase freshness of products contained.

| Additive | Amount |
| --- | --- |
| PVC | <500 ppm |
| Color additive (black, TiOx) | <1000 ppm |
| Barrier Material (PETG) | <6500 ppm |
| Antimony | <500 ppm |
| Acetaldehyde | By blend |
| Boron | <1000 ppm |
| Nucleating agents | <20% crystalline |
| Polymers that phase separate | Depends on size of phase |
| Light stabilizers | WI > 35 |
| Antioxidants | Master batch by blend |
| Residual acids from adhesives | <0.5 g/in$^2$ |

Example compounds and loading affecting product quality and freshness.

Compound Loading Adjustment Based on Absorption, Thermal and Physical Behavior

Compound loading to maximize performance and develop standards for recycled thermoplastics (% RPET) was determined using the "best" subsets of predictors of % RPET from a set of 17 potential indicators. The analysis proceeded in two steps: the first step identified the subset of variables that were independent of the silicone coating, a nuisance factor. From the derived subset, the second step identified the best subsets of predictors of % RPET that maximize performance and ranges.

Determination of Independent Subset

The first task was to identify a subset of predictor variables that were independent of the nuisance factor, the silicone coating. For this purpose, the silicone variable was scored 1=coating and 0=no coating and used as the dependent variable in a binary logistic model as described, by way of example, in Cox, D. R. "The Continuity Correction" *Biometrika* 57:217-219 (1970) and Cox et al., Theoretical Statistics (Chapman and Hall, London) (1974), the disclosures of which are hereby incorporated herein by reference in their entirety. To accomplish this objective, the efficient score as disclosed in Rao, C. R., "Linear Statistical Inference and its Applications," 2nd ed., New York: Wiley (1973), which is hereby incorporated herein by reference in its entirety, was obtained for the 17 indicators (Table 3).

Table 3: Mean, SD, and Statistical Significance of the Coating Treatment

TABLE 1

Means, SD, and Statistical Significance of the Coating Treatment

| Variable | Mean | SD | λ-Score | Prob. |
| --- | --- | --- | --- | --- |
| Hc | 24.49 | 1.4 | 12.754 | <0.001 |
| Tg | 83.26 | 2.18 | 12.467 | <0.001 |
| Hm" | 30.77 | 3.38 | 11.756 | <0.001 |
| Tcwidth | 13 | 2.07 | 7.815 | 0.005 |
| Tm"offset | 254.38 | 1.16 | 6.687 | 0.01 |
| DEGContent | 4.09 | 0.21 | 4.902 | 0.027 |
| Tm" | 248.5 | 1.18 | 4.902 | 0.027 |
| TgReverse | 74.82 | 1.65 | 3.544 | 0.06 |
| Hm' | 34.83 | 2.13 | 2.879 | 0.09 |
| Tcoffset | 144.16 | 3.48 | 1.318 | 0.251 |
| Tconset | 131.16 | 1.91 | 0.895 | 0.344 |
| Tm"onset | 227.89 | 3.05 | 0.707 | 0.4 |
| Crystal | 8.99 | 1.71 | 0.496 | 0.481 |
| Tm' | 251.67 | 1.38 | 0.108 | 0.742 |
| Tc | 137.55 | 2.06 | 0.032 | 0.859 |
| Tm"width | 26.49 | 2.5 | 0.03 | 0.863 |
| A350 nm | 1.56 | 0.15 | 0.003 | 0.958 |

Rao's efficient score, λ, measures the initial contribution a variable makes in predicting an outcome; it is commonly used as an initial screen in forward selection algorithms. In typical forward selection algorithms, if a potential predictor has a sufficiently significant λ-score; it becomes eligible for further analysis. However, in the current study the goal was to identify indicators that were independent of the nuisance factor; thus, non-significant linear combinations of indicators were sought. In line with this objective, the eight variables reported in Table 3 with λ-scores with p>0.10 were flagged as potentially independent of the nuisance factor, the silicone coating. To identify the linear combination of variables, independent of a silicone coating, the systematic "directed search" selection method of Daniel et al., "Fitting Equations to Data: Computer Analysis of Multifactor Data," J. Wiley and Sons, New York, N.Y. (1980), the disclosure of which is hereby incorporated herein by reference in its entirety, was adapted as follows: Variables with the smallest λ-scores (high p values) were entered into the binary logistic regression one at a time. After each entry, a xx2 test for linear dependence and the Cox-Snell RR2 were calculated. This process stopped when a statistically significant linear combination was obtained (Table 4).

TABLE 4

Variable Subsets and Test Statistics

| Predictor | $x^2$ | df | prob. | $R^2$ |
| --- | --- | --- | --- | --- |
| A350 nm | 0.003 | 1 | 0.958 | 0.000 |
| Tm"width | 0.042 | 2 | 0.979 | 0.001 |
| Tc | 0.274 | 3 | 0.965 | 0.005 |
| Tm' | 0.719 | 4 | 0.949 | 0.012 |
| % Crystal | 3.186 | 5 | 0.671 | 0.052 |
| Tm"Onset | 18.859 | 6 | 0.004 | 0.270 |

The systematic test of nested variables revealed five variables that were independent of the nuisance factor: A350 nm, Tm" width, Tc, Tm', and % Crystal. The linear combination independence requirement breaks down when the sixth variable, Tm" onset, is entered in the binary logistic regression, xx2=18.86, df=6, p=0.004, and the Cox-Snell RR2=0.27 (Table 4).

Table 5: Model Fit Statistics for all Possible Subsets

TABLE 3

Model Fit Statistics for All Possible Subsets

|  | Deviance | Scale | $x^2$ | Relative AICc | BIC |
|---|---|---|---|---|---|
| df = 54 | | | | | |
| A350 nm, Tm"width, Tc, Tm', Crystal | 49.2 | 0.9 | 40.6 | 3.2 | 24.4 |
| df = 55 | | | | | |
| A350 nm, Tm"width, Tc, Tm' | 49.3 | 0.9 | 40.7 | 1.3 | 15.9 |
| A350 nm, Tm"width, Tc, Crystal | 52.0 | 0.9 | 42.6 | 4.0 | 18.6 |
| A350 nm, Tm"width, Tm', Crystal | 49.8 | 0.9 | 41.2 | 1.8 | 16.3 |
| A350 nm, Tc, Tm', Crystal | 55.0 | 1.0 | 43.7 | 7.0 | 21.6 |
| Tm"width, Tc, Tm', Crystal | 99.3 | 1.8 | 89.1 | 51.3 | 65.9 |
| df = 56 | | | | | |
| A350 nm, Tm"width, Tc | 52.3 | 0.9 | 43.0 | 2.4 | 10.2 |
| A350 nm, Tm"width, Tm' | 50.0 | 0.9 | 41.3 | 0.0 | 7.9 |
| A350 nm, Tm"width, Crystal | 52.6 | 0.9 | 43.2 | 2.6 | 1.5 |
| A350 nm, Tc, Tm' | 56.2 | 1.0 | 44.4 | 6.2 | 14.0 |
| A350 nm, Tc, Crystal | 55.8 | 1.0 | 44.7 | 5.8 | 13.6 |
| A350 nm, Tm', Crystal | 56.9 | 1.0 | 45.2 | 6.9 | 14.8 |
| Tm"width, Tc, Tm' | 138.6 | 2.5 | 118.2 | 88.6 | 96.5 |
| Tm"width, Tc, Crystal | 106.0 | 1.9 | 91.7 | 56.0 | 63.9 |
| Tm"width, Tm', Crystal | 158.6 | 2.8 | 145.7 | 108.6 | 116.5 |
| Tc, Tm', Crystal | 113.7 | 2.0 | 99.4 | 63.7 | 71.5 |
| df = 57 | | | | | |
| A350 nm, Tm"width | 53.1 | 0.9 | 43.7 | 1.1 | 2.2 |
| A350 nm, Tc | 57.0 | 1.0 | 45.5 | 5.0 | 6.2 |
| A350 nm, Tm' | 58.8 | 1.0 | 46.3 | 6.8 | 7.9 |
| A350 nm, Crystal | 57.6 | 1.0 | 46.0 | 5.6 | 6.7 |
| Tm"width, Tc | 156.7 | 2.7 | 130.5 | 104.7 | 105.9 |
| Tm"width, Tm' | 408.4 | 7.2 | 335.5 | 356.4 | 357.6 |
| Tm"width, Crystal | 170.6 | 3.0 | 153.7 | 118.7 | 119.8 |
| Tc, Tm' | 209.3 | 3.7 | 169.7 | 157.3 | 158.4 |
| Tc, Crystal | 116.2 | 2.0 | 100.3 | 64.3 | 65.4 |
| Tm', Crystal | 160.5 | 2.8 | 145.8 | 108.5 | 109.6 |
| df = 58 | | | | | |
| A350 nm | 59.5 | 1.0 | 47.3 | 5.5 | 0.0 |
| Tm"width | 561.5 | 9.7 | 444.7 | 507.5 | 501.9 |
| Tc | 218.6 | 3.8 | 174.9 | 164.6 | 159.1 |
| Tm' | 515.2 | 8.9 | 409.6 | 461.2 | 455.7 |
| Crystal | 170.7 | 2.9 | 153.9 | 116.7 | 111.1 |

Generalized Logit Model

Generalized linear modelling, GZLM, is a general method allowing for various model types. The current model is a generalized logit model, one with a Binomial prior and a uniform observed data distribution. The posterior is a mixture of the two distributions.

For the present data set ($Y_i$, $X_i$, $w_i$) the following definitions apply, $i=1, \ldots, n$ denotes the 60 observations, $Y_i$ is a prior binomial count corresponding to % RPET, $X_i$ is the vector of the predictor variables (Table 2), and $w_i$ is the observed data weight for criterion $Y_i$. The goal of the analysis was to identify the "best" subsets of % RPET predictors. For this purpose the generalized logit model for extra-binomial variation was employed.

The current experiment has six levels of $Y_i$ (% RPET): 0, 20, 40, 60, 80, 100% and to denote the number of observations, $i=1, 2, \ldots, n$. $Y_i$ is the imaginary prior count of the number of "successes" out of $m_i=m=100$ trials. For each of the six levels of % RPET there are 10 observations for a total of $n=60$ observations. Following William's (1982) model II, the expected value and variance are given as:

$$E(Yi) = m\pi i \qquad [2]$$

$$\text{Var}(Yi) = \varphi w i^{-1} m \pi i(1-\pi i) \qquad [3]$$

where $\varphi w_i^{-1}$ represents the extra-binomial variation, $\varphi$ is given by $[1+\rho(m-1)]$, and where $\rho$ is a parameter that may be interpreted as the correlation between the binary components; $w_i^{-1}$ is the scale weight. We assume constant $\rho$ for all proportions. The goal of the analysis was to identify the "best" subsets of % RPET predictors. For this purpose, a generalized logit model for extra-binomial variation was employed.

The generalized logit model is defined by two functions g and v and the link function $g(\pi i) = \eta i$ is a monotonic differentiable link function relating the mean probability (or binomial proportion) $\pi i = E(Y_i/m)$ to the linear predictor $\eta = X\beta$ where X is an n×p design matrix, $\beta$ is a p×1 vector of regression coefficients. The variance function vv relates the variance with the expected binomial count, $m\pi i$, to the variance by $\text{Var}(Yi) = \phi w^{-1} v(\pi i)$ where $\phi = m\varphi$. For the binomial distribution $v(\pi i) = \pi i(1-\pi i)$ so the scale factor $\varphi = 1$ and $w i = 1$ under ideal binomial conditions. In this experiment, however, the observed values for $Y_i$ are uniformly distributed over six levels: 0, 20, 40 60, 80, and 100; thus, the observed data weight reflects a uniform distribution, $w i = \frac{1}{6}$.

The five potential predictors (Table 4) were studied in the following analysis. The generalized logit model was defined as the following link-linear function:

$$\eta i = g(\pi i) = \Sigma j \beta j x i j, \; i=1, \ldots, n. \qquad [4]$$

with the logit link function g such that, $$E(Yi/m) = \pi i = g^{-1}\left(\ln\left[\frac{\pi_i}{1-\pi_i}\right]\right), \qquad [5]$$

$$\text{Where, } \Sigma \beta j x i j = \ln\left(\frac{\pi_i}{1-\pi_i}\right) \qquad [6]$$

The Best Subsets

From the five eligible variables (Table 4), the next step identified the "best" subsets. The five variables give 26 subset models; each is evaluated using the Bayesian information criterion, BIC, and the finite sample corrected Akaike Information Criterion, AICc.

$$BIC = -2*(L) + k*\ln(n*m), \qquad [7]$$

$$AICc = -2*(L) + \frac{2k(n*m)}{(n*m) - k - 1}, \qquad [8]$$

where L is the log likelihood function, kk=pp+1 is the number of predictors plus the intercept in the model, nn is the number of observations and mm is the number of trials. BIC and AICc were used as the information criteria to evaluate the relative quality of the generalized logit models as disclosed in Akaike, H. "Maximum Likelihood Identification of Gaussian Autoregressive Moving Average Models," Biometrika 60(2):255-265. (1973); Schwarz, G., "Estimating the Dimension of a Model." The Annals of Statistics 6(2):461-464 (1978); and Anderson et al., "Avoiding Pitfalls When Using Information-Theoretic Methods," The Journal of Wildlife Management 66:912-918 (2002), the disclosures of which are hereby incorporated herein by reference in their entirety.

The information criteria (Table 5) are given relative to the minimum, where min AICc=90.11 and min BIC=109.5;

smaller relative scores indicate better fit. BIC and AICc tend to move together, but each emphasizes different aspects of the model. BIC tends to favor models with less predictor variables (George, 2000). In the current data set, the best model by BIC is the single predictor A350 nm, and the best model by AICc is the three variable model: A350 nm, Tm" width, and Tm'. The best two variable model is A350 nm and Tm" width.

Assessment of Changes in Nutritive Value of Selected Vegetables

Converted sheet were thermoformed into retail packaging and used to assess changes in the nutritive value of specific vegetables during prolonged storage. Changes were correlated to the clarity and permeation characteristics of the plastics. All packages were stored in controlled-environment rooms equipped with 2 banks of fluorescent lights. Light intensity at the package surface was measured as Lux using a quantum light meter. Nutritive changes were assessed as decreases in Vitamin C, β-carotene, and chlorophyll during simulated retail distribution and display, up to 21 days after packaging.

Ascorbic Acid (Vitamin C)

Free ascorbic, dehydroascorbic (DHA), and total ascorbic (TA) acid content was determined for pre-cut Romaine lettuce using High Performance Liquid Chromatography (HPLC). Initial storage was 5 days at 3.3° C., 80% R.H. in the dark, followed by placement of half the samples at 5° C., 80% R.H under constant light, while half the samples remained at this same temperature in total darkness. The temperature/light regime was based on the observed environments for pre-cut products shipped from California to the East Coast as discussed in Zeng et al. "Growth of *Escherichia coli* O157: H7 and *Listeria monocytogenes* in Packaged Fresh-Cut Romaine Mix at Fluctuating Temperatures During Commercial Transport, Retail Storage, and Display," Journal of Food Protection® 77(2):197-206 (2014), the disclosure of which is hereby incorporated herein by reference in its entirety. In most cases, relative humidity during shipping, distribution, and retail display is not controlled; however, it was controlled in this study to prevent excessive dehydration of tissues during storage. Packages were sampled at 0, 5, 8, 11, 14, 17, and 21 days of storage.

HPLC analysis was performed following the method reported by Chebrolu et al. "An Improved Sample Preparation Method for Quantification of Ascorbic Acid and Dehydroascorbic Acid by HPLC," LWT-Food Science and Technology 47(2):443-449 (2012), the disclosure of which is hereby incorporated herein by reference in its entirety. A 2 g sample of tissue was extracted with an equal weight of metaphosphoric acid (MA) (3 g/100 ml DI water), using a tissue homogenizer. The sample was centrifuged at 4500 revolutions per minute for 10 minutes after which the supernatant was passed through a 0.45 µm syringe filter in preparation for HPLC analysis. Likewise, tris(2-carboxy ethyl) phosphine hydrochloride (TCEP) was used to reduce DHA to ascorbic acid to determine DHA and total ascorbic acid content of the samples. A 2 g sample was treated with an equal weight of 3 g/100 ml MA, homogenized, and centrifuged. A 300 µL aliquot was treated with 300 of 5 mmol/L TCEP, incubated for 30 min, then filtered through a 0.45 µm filter before injection on the HPLC. The sample DHA level was calculated as the difference between free AA and TA.

The HPLC used was a Shimadzu HPLC system equipped with photodiode array and C18 spherisorb column (150 mm×4.6 mm i.d. and 3 µm particle size) held at 25° C. The primary detection wavelength was 254 nm. Runs were performed isocratically using 0.01 mol/L dihydrogen ammonium phosphate (pH 2.6) as the mobile phase. Flow rate was 1 ml/min. Standards of 1 to 10 mg ascorbic acid/100 ml MA solution were prepared from a stock solution of 100 mg ascorbic acid/100 ml MA and were used to construct a calibration curve. The concentration of ascorbic, dehydroascorbic, and total ascorbic acid in the samples were expressed as mg per 100 g fresh weight lettuce. Percent recovery was determined by taking two 10.00 g samples of lettuce from a lettuce head. One sample was spiked with 0.1 g ascorbic acid. Both samples were prepared and analyzed using the procedure described above. This procedure was repeated 4 times.

Pro-Vitamin A (β-Carotene)

Pre-cut sweet potatoes were used as a model system. They are high in β-carotene and do not contain related carotenoids, such as chlorophyll, that would require excessive processing to remove. The potatoes were stored as smooth-cut chips, julienned strips ("matchsticks"), fry-sized wedges, and ~½" diced pieces. Pre-cut potatoes were treated with 100 ppm active chlorine at pH 6.5 before being packaged to reduce decay during storage. Initial storage was 5 days at 3.3° C., 80% R.H in the dark, followed by placement of half the samples at 5° C., 80% R.H under constant light, and half the samples at this same temperature in total darkness. Packages were sampled at 0, 5, 8, 11, 14, 17, and 21 days of storage and unwashed potatoes were sampled at Day 0, as well.

Beta-carotene was extracted using hexane and quantified spectrophotometrically as discussed in Picha, D. H., "HPLC Determination of Sugars in Raw and Baked Sweet Potatoes." Journal of Food Science 50(4):1189-1190 (1985), the disclosure of which is hereby incorporated herein by reference in its entirety. Peeled sweet potatoes were initially puréed using a small, table-top food processor. A 0.5 g sample of the purée was extracted for 1 min with 10 ml of HPLC-grade hexane, using a tissue homogenizer. The homogenate was filtered through Whatman #1 paper into a 50 ml volumetric and additional hexane was added to yield a final volume of 50 ml. The absorbance of 3 ml of sample was immediately read at 440 nm. A β-carotene calibration curve was prepared using 99.5% pure β-carotene. Results were expressed as mg β-carotene/100 g fresh weight. β-Carotene makes up 86 to 90% of the carotenes present in sweet potatoes, so changes at this wavelength were correlated with changes in the nutritive value of the roots.

Chlorophyll

Previous research indicated that chives, when exposed to fluorescent light, yellowed and senesced at a much faster rate than chives stored in darkness. Since the reduction in chlorophyll is so dramatic, chives were used as the model system for this work. Initial storage was 5 days at 3.3° C., 80% R.H. in the dark, followed by placement of half the samples at 5° C., 80% R.H under constant light, and half the samples at this same temperature in total darkness. Punnets were sampled at 0, 5, 8, 11, 14, 17, and 21 days of storage.

To prevent the photodegradation of chlorophyll, all glassware was covered with aluminum foil. From each sample 25 g of chives was weighed and placed in a blender. The tissue was homogenized for 1 min with 50 ml of deionized water. Ten grams of homogenized tissue was weighed into a beaker and 50 ml of 80% acetone:water (v/v) added as disclosed in Yamauchi et al., "Chlorophyll and Xanthophyll Changes in Broccoli Florets Stored Under Elevated CO2 or Ethylene-Containing Atmosphere," *HortScience* 33(1):114-117 (1998) and Yamauchi et al., "Ascorbic Acid and Beta-Carotene Affect the Chlorophyll Degradation in Stored Spinach (*Spinacia oleracea* L.) Leaves," *Food Preservation Science* 24(1):17-21 (Japan) (1998), the disclosures of which are hereby incorporated herein by reference in their entirety.

The sample was allowed to rest for 10 min. The extract was filtered through Whatman P8 filter paper using a vacuum system. Two 10 ml aliquots of 80% acetone:water were used to rinse the extraction beaker and solids remaining on the filter paper to ensure full extraction of the chlorophyll. The filtrate was further clarified by passing it through a non-reactive PTFE 0.45 µm syringe filter. Total chlorophyll was measured using a spectrophotometer set at 645 nm.

Example 2

Materials and Methods
Sample Preparation:
Virgin PET resin and washed post-consumer (PC)-PET flake were blended utilizing an industrial extruder to produce 0, 25, 50, 75, and 100% PCR-PET by weight. Briefly, washed post-consumer flake was transferred via vacuum lines to a Con Air crystallizer and crystallized for 45 minutes utilizing an air temperature of 155° C. The crystallized PC-flake was blended with virgin resin in an AEC Whitlock OS series blender then transferred to a Con Air carousel drier; the blended material was dried for four hours at 140° C. with a −40° C. dew point. The dried material blend was transferred to a Reifenhauser single screw extruder with a screw L/D ratio of 32:1 and extruded with a screw speed of 80 rpm. Film thicknesses for each sheet blend ranged between 18 mil and 20 mil (0.457 mm and 0.508 mm, respectively).

Absorption Spectroscopy:
Film samples were fitted into a custom made clamp measuring 12.7 cm×8.5 cm×2.3 cm. Ultraviolet-visible (UV-vis) spectra were collected between 200 nm and 500 nm in absorbance mode using a Tecan Safire spectrometer (Zurich, Switzerland). Specimen thicknesses were measured with a Mitutoyo IP 65 electronic digital micrometer (Kawasaki, Japan). Each specimen clamp was inserted into the sample chamber such that the specimen was aligned perpendicular to the incident irradiation. Each UV-vis absorbance value measured along the spectrum was divided by the thickness of the specimen to account for differences in path length attributed to the variations in the thickness of each specimen between specimens.

Vibrational Spectroscopy:
Attenuated total reflectance-Fourier transform infrared (ATR-FTIR) spectra were collected with a Nicolet 380 Infrared spectrometer at ambient temperature (Waltham, Mass.), fitted with a diamond crystal stage. The spectrum of each specimen was collected with 64 scans and a resolution of 2 cm-1.

Raman spectra were collected at ambient temperature on an XploRa Plus confocal Raman microscope (Horiba Scientific/JY, France) using a 100× magnification, 0.90 numerical aperture microscope objective. Each spectrum was comprised of three exposures with ten seconds per exposure and a resolution of 2 cm$^{-1}$. The excitation wavelength was 532 nm with a laser power of 10 mW. Each spectrum was baseline corrected and the changes in area of each functional group characteristic band was calculated after normalization to the area of the 705 cm$^{-1}$ band according to the procedure (equation 1) described in Richard-Lacroix et al., "Orientation and Structure of Single Electrospun Nanofibers of Poly(ethylene terephthalate) by Confocal Raman Spectroscopy." *Macromolecules* 45:1946-53 (2012), the disclosure of which is hereby incorporated by reference in its entirety.

$$A(v)_{subtracted} = A(v)_{\% RPET} - A(v)_{virgin PET} \quad (1)$$

Fluorescence Spectroscopy:
Fluorescence intensity measurements were collected with a Tecan Safire fluorometer (Zurich, Switzerland). Scans were performed in 3D fluorescence mode with excitation and emission wavelengths ranging from 300 nm to 600 nm in 5 nm increments at a gain of 75. The z-position was held fixed at 11,020 nm.

Statistical Analysis: Investigations for linear relationships and the statistical significance of trendline slopes between data sets were performed by calculating the Pearson product moment correlation coefficient and linear regression analysis, respectively, via Minitab 17 software utilizing a 95% confidence ($\alpha=0.05$) as described in Ellison, Practical Statistics for the Analytical Scientist: A Bench Guide. 2nd Ed. Cambridge: The Royal Society of Chemistry (2009), which is hereby incorporated by reference in its entirety. Statistical comparison between trendline slopes of the current data and the previous work described in Curtzwiler et al., "Effect of Recycled Poly(ethylene terephthalate) Content on Properties of Extruded Poly(ethylene terephthalate) Sheets," J. Plast. Film Sheeting 27:65-86 (2011), which is hereby incorporated by reference in its entirety, was conducted by determining the interaction effect as described in Gelman, Data Analysis Using Regression and Multilevel/Hierarchical Models, New York, N.Y.: Cambridge University Press (2007).

Figures 12A, 12B, 12C:
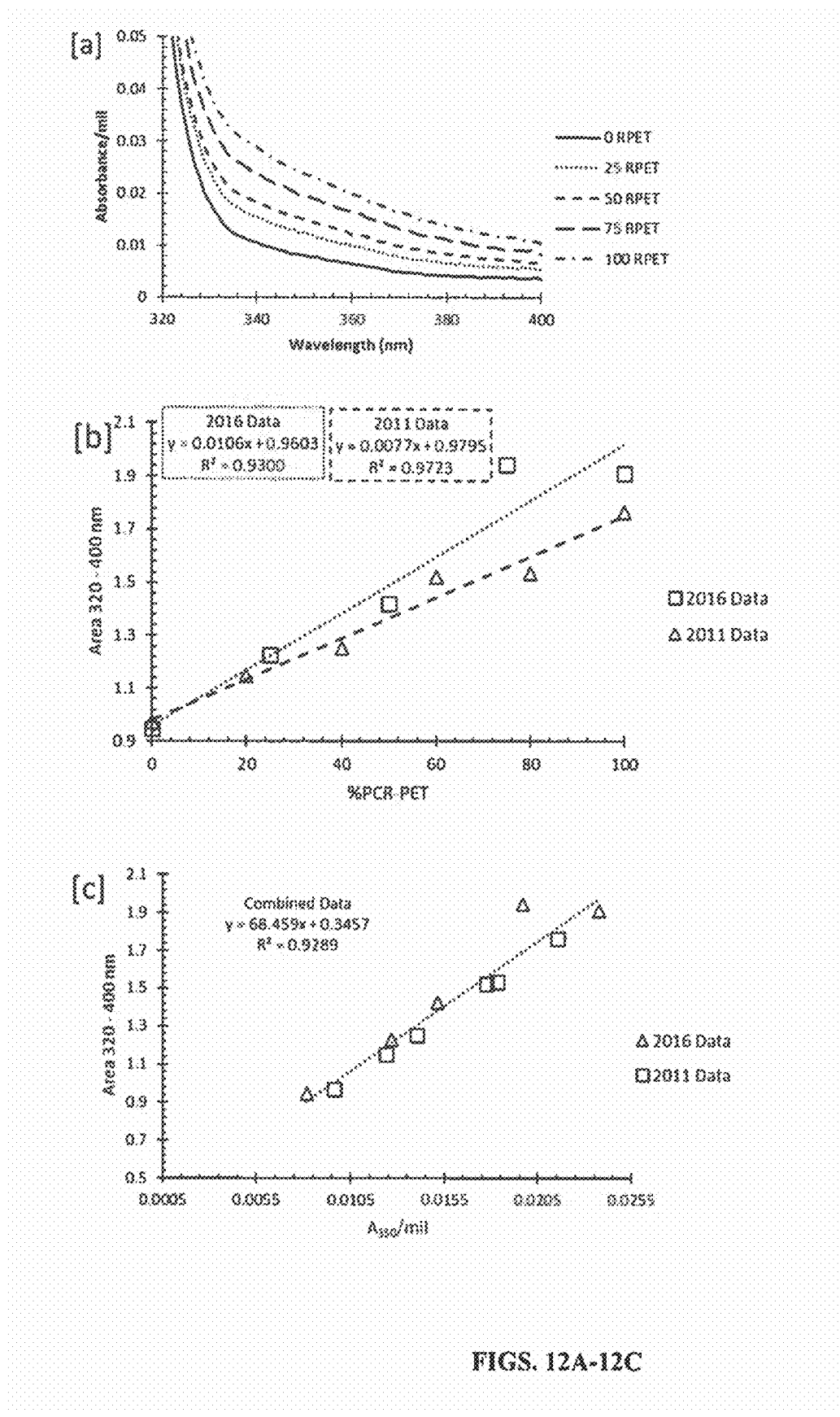
FIGS. 12A-12C illustrate a UV-Vis spectra of polyethylene terephthalate sheets with increased PCR-PET content (FIG. 12A), a change in UVA absorbance potential from virgin PET resin for PCR-PET blends for data collected in 2016 and 2011 (FIG. 12B), and a graph showing a linear relationship between the thickness normalized absorbance at 350 nm and the UVA absorption potential (FIG. 12C).
Figures 13A, 13B, 13C, 13D, 13E:
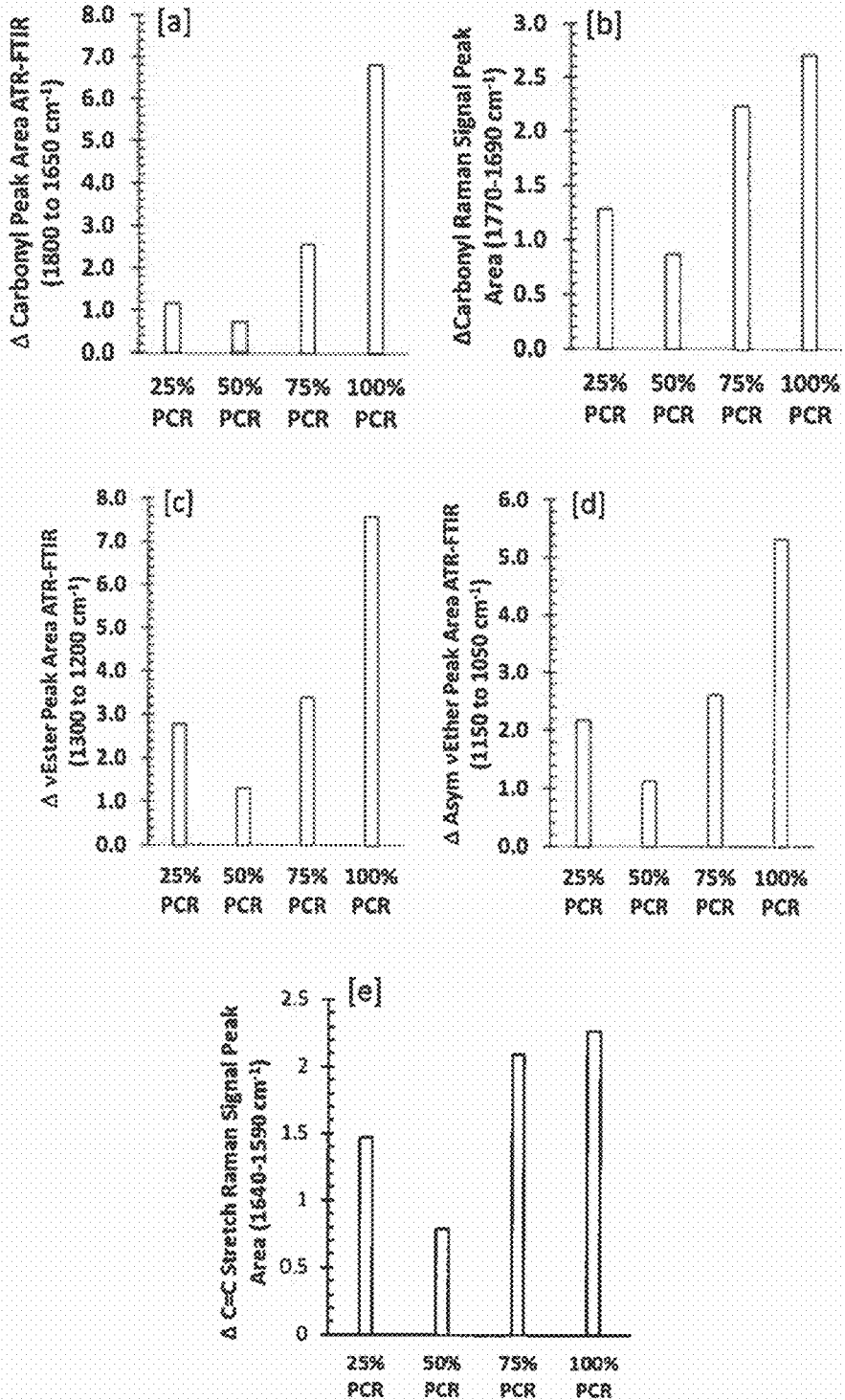
FIGS. 13A-13E are graphs showing calculated peak area changes due to increasing PCR-PET blending with virgin PET material carbonyl peak area results (ATR-FTIR) (FIG. 13A), carbonyl peak area results (Raman) (FIG. 13B), ester peak area (ATR-FTIR) (FIG. 13C), asymmetric ether peak area results (ATR-FTIR) (FIG. 13D), and C=C stretch (Raman) (FIG. 13E).

Results
Ultraviolet Visible Spectroscopy:
Virgin and PCR-PET polymer intrinsically absorbs UV radiation at wavelengths between 280 and 320 nm, which saturated the absorption detector utilizing the sample thickness (~20 mil), common for packaging applications as shown in FIG. 12A. Therefore, this region of the UV spectrum will not be discussed in reference to PCR-PET blend concentrations. The UVA absorption potential for each PCR-PET blend ratio was quantified and defined as the area under the thickness-normalized absorbance spectrum between 320 and 400 nm (UVA region; FIG. 12A). The UVA absorption potential increased linearly with increasing PCR content in the PCR-PET blend as shown in FIG. 12B and the data indicated that utilizing 100% PCR-PET polymer increased the UVA absorption by ~100% for the current study and ~80% in the previous work described in Curtzwiler et al., "Effect of Recycled Poly(ethylene terephthalate) Content on Properties of Extruded Poly(ethylene terephthalate) Sheets," J. Plast. Film Sheeting 27:65-86 (2011), compared to the virgin resin as shown in FIG. 1B. No significant difference was determined between the data sets collected in 2011 and the data reported here for the UVA absorption potential as a function of PCR-PET concentration trendline slopes ($p=0.129$) nor the constant ($p=0.09$) of the regression equation (FIG. 12B), indicating the reproducible nature of UVA absorption properties for PCR-PET blends.

The thickness-normalized absorption at 350 nm was additionally evaluated as a potential single point measurement to predict the UVA absorption potential as defined above. Pearson's product moment correlation coefficient indicated a linear relationship between the A350 nm/mil and the UVA absorption potential for both the 2011 and 2016 data sets independently ($p<0.001$ and $p=0.009$, respectively). Regression analysis and investigation of the interaction effect of when the data were collected (2011 compared to 2016) indicated that there was no statistical difference between the trendline slopes (66.96 for 2011; 68.91 for 2016; p=0.873), and thus, values from both data sets (2011 and 2016) were combined and utilized to produce a regression equation capable of providing a single measurement investigation of the UVA absorption potential (R2=0.9289; Equation 2, FIG. 12c); such an equation increases the viability using a single point, continuous measurement to monitor the UVA absorption performance of PCR-PET blends and provides a quality control calibration parameter for adjusting the composition in real-time.

$$UVA \text{ Absorption Potential} = 68.46 \frac{A_{350 \, nm}}{mil} + 0.346 \quad (2)$$

Vibrational Spectroscopy:

Understanding and determining the mechanism of increased UV absorbance would enable converters and recyclers to reproducibly tailor blend compositions and processing parameters to selectively control the ultraviolet and visible light absorption properties. Accordingly, the molecular composition of each PCR-PET blend was investigated by vibrational spectroscopic methods. Both ATR-FTIR and Raman spectra indicated an overall decrease in carbonyl concentration for specimens containing PCR as shown in FIGS. 13A-13E. This is attributed to the loss of acetaldehyde/benzaldehyde degradation byproducts as described in Samperi et al., "Thermal Degradation of Poly (ethylene terephthalate) at the Processing Temperature," *Polymer Degradation and Stability*, 83:3-10 (2004) and Holland, et al., "The Thermal Degradation of PET and Analogous Polyesters Measured by Thermal Analysis—Fourier Transform Infrared Spectroscopy," *Polymer*, 43:1835-47, which are hereby incorporated by reference in their entirety.

However, these spectroscopic methods do not easily differentiate carbonyl types, thus, quantification of the carbonyl decrease due to the loss of aldehyde species is confounded by the formation of quinone derivatives on the terephthalate constituents as described in Romão et al., "Poly (ethylene terephthalate) Thermo-Mechanical and Thermo-Oxidative Degradation Mechanisms," *Polymer Degradation and Stability* 94: 1849-59 (2009) and MacDonald, "New Advances In Poly(ethylene terephthalate) Polymerization and Degradation," *Polymer International*, 51: 923-30 (2002), which are hereby incorporated by reference in their entirety. A reduction in the asymmetric ether stretch frequency at 1095 $cm^{-1}$ was also observed, which may be due to the degradation of the diethylene glycol substituents in the PET backbone (FIGS. 13A-13E). It is noted that the reduction of the ester stretch peak area from 1300 to 1200 $cm^{-1}$ was similar to the carbonyl decrease and can be attributed to the concerted degradation mechanism through an unstable β-chain scission intermediate.

The reduction of the carbonyl, ester, ether, and C=C functional groups as a function of PCR concentration deviated from linearity for the 50% PCR-PET blend as determined via ATR-FTIR and Raman spectroscopy (FIGS. 13A-13E). This suggests that the 50% PCR-PET blend samples has unique material properties that differ from the other blend ratios. At 50 wt % PCR-PET there is a 1:1 mass ratio between the virgin resin and PCR resin, but not a 1:1 molar ratio with respect to the average molecular weight and polydispersity. It is well established in the literature that melt processing decreases the molecular weight of PET polymer due to the thermal and mechanical forces acting on the polymer during processing as discussed in Andrassy et al., "Molecular Mass Distribution Changes During Processing of Poly(ethylene terephthalate)," *Polymer degradation and stability*, 41: 77-81 (1993), Awaj a et al., "Recycling of PET," *European Polymer Journal*, 41: 1453-77 (2005), and Incarnato et al., "Structure and Rheology of Recycled PET Modified by Reactive Extrusion," *Polymer*, 41: 6825-31 (2000), which are hereby incorporated by reference in their entirety.

Figure 14:
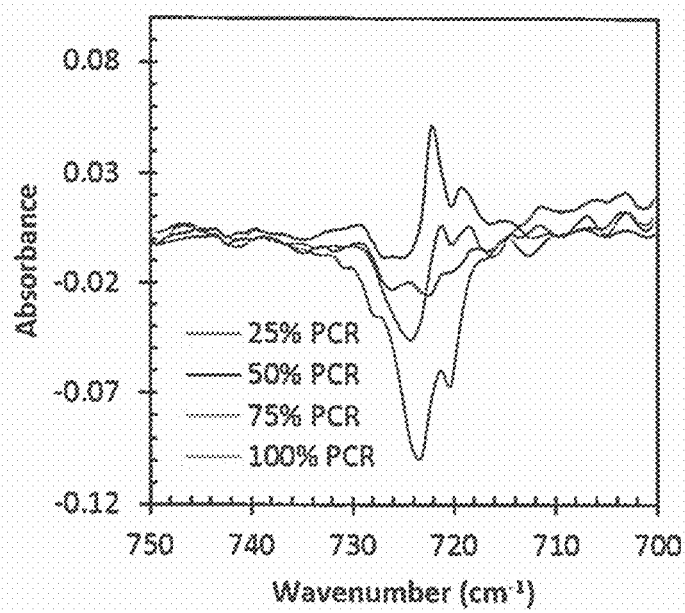
FIG. 14 is a graph showing virgin PET subtraction spectroscopy of PCR-PET blends using ATR-FTIR of 730 to 710 $cm^{-1}$ region specific for $(CH_2)n$-$CH_3$ chain deformation, end group rotation, and aliphatic crystallinity.

During melt processing of the material, it is possible that the dissimilar molecular weight molar ratio between the virgin material and the PCR-PET creates heterogeneity in the material (e.g., phase separation/domains of various molecular weights or less perfect crystalline structures). Since PCR-PET has a higher crystalline fraction than virgin PET under the same extrusion/take up conditions (as measured via differential scanning calorimetry) as discussed in Curtzwiler et al., "Effect of Recycled Poly(ethylene terephthalate) Content on Properties of Extruded Poly(ethylene terephthalate) Sheets," *J Plast Film Sheeting*, 27: 65-86 (2011), which is hereby incorporated by reference in its entirety, heterogeneity would result in a preferential segregation of PCR-PET forming a heterogeneous mixture of each material in the final blend, which would be most noticeable at 50 wt % PCR-PET. The resulting dispersion would result in more stability of the aromatic ring through ordered structure, and a greater crystalline fraction in the CH2 deformation vibration between 720 and 725 $cm^{-1}$. Analysis of the crystalline fraction of the 50 wt % PCR-PET via ATR-FTIR revealed an increase in the concentration of the crystalline fraction over that in virgin PET resin and the other PCR-PET samples. The increase in the crystalline $CH_2$ deformation domain supports the possibility of a heterogeneous dispersion with the 1:1 blend ratio as illustrated in FIG. 14.

Fluorescence Spectroscopy:

Thermo-mechanical processing/reprocessing of PET induces main chain and end group degradation that results in the production of fluorescent quinone derivatives due to radical attack of the terephthalic acid aromatic ring as described in MacDonald, "New Advances in Poly(ethylene terephthalate) Polymerization and Degradation," *Polymer International*, 51: 923-30 (2002), which is hereby incorporated by reference in its entirety. A strong coefficient of determination (R2=0.9878) was determined between the absorbance at 350 nm (UV-Vis spectroscopy) and the fluorescence intensity at 501 nm (ex 350 nm), suggesting that the moiety causing the increased absorbance at 350 nm (as noted in FIGS. 12A-12C) is due to the quinone derivatives formed during degradation processes. This trend is expected as increasing PCR content increases the mass fraction of material that has undergone multiple melt processing steps increasing the potential for degradation reactions. Although this study proposes that fluorescence properties with an excitation wavelength of 350 nm and emission at 501 nm are due to the quinone derivatives, the 3D fluorescence scans revealed that these conditions do not represent the fluorescence intensity maximum for each PCR-PET blend.

Figure 15:
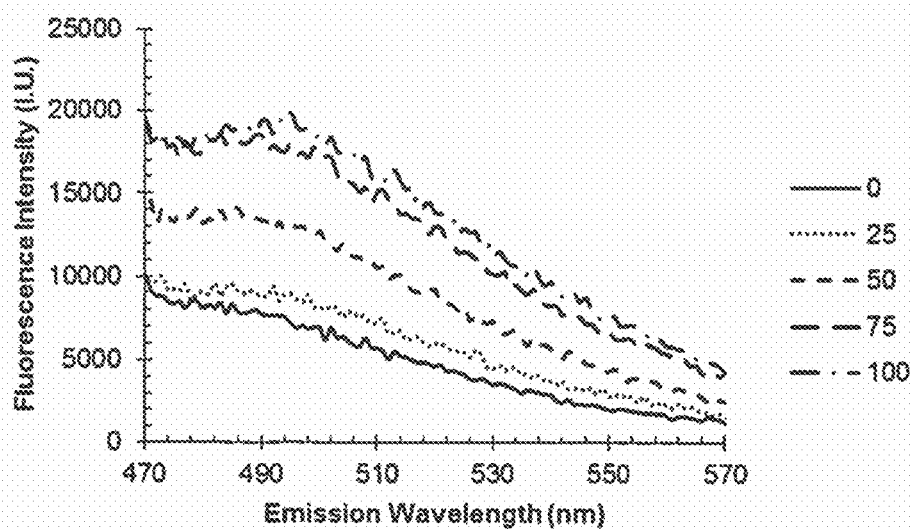
FIG. 15 shows fluorescence emission spectra (excitation wavelength of 350 nm) of polyethylene terephthalate sheets as a function of percent post-consumer content.
Figure 16:
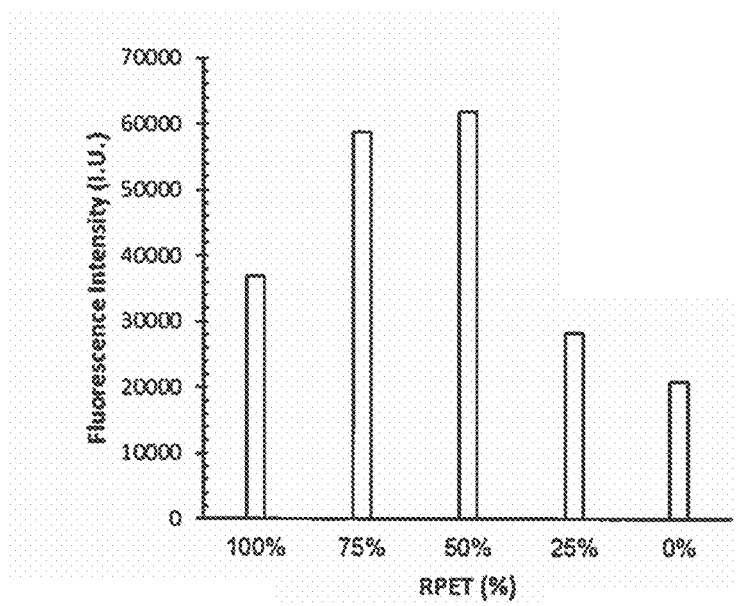
FIG. 16 shows peak fluorescent intensities from the 3D fluorescence scans. Intensities were recorded at an excitation of 335 nm and emission of 395 nm.

3D fluorescence scans were utilized to identify the peak fluorescent intensity of each PCR-PET blend as shown in FIG. 15. The highest fluorescence intensity maximum for all PET samples occurred at an excitation wavelength of 335 nm and an emission wavelength of 395 nm. Increased fluorescence under these excitation and emission parameters have been previously attributed to the formation of dimers due to intramolecular interactions of non-nearest neighbor phenyl rings or intermolecular interactions between adjacent chains resulting in dimers as described in Sonnenschein et al., "Absorption and Fluorescence Spectra of Poly(ethylene terephthalate) Dimers," *Polymer*, 31: 2023-60 (1990) and Dodge et al., "Conformation of the Ground-State Dimer in Poly(ethylene terephthalate)," *Journal of Polymer Science Part B: Polymer Physics*, 31: 207-12 (1993), which are incorporated by reference in their entirety. While it was anticipated that increasing PCR-PET content would increase the observed peak fluorescent intensity due to the formation of more quinone derivatives, the 50 wt % PCR-PET blend as shown in FIG. 16, possessed the highest peak intensity among all measured content which is inversely proportional to the trends noticed via Raman and ATR-FTIR spectroscopies; despite the UVA absorption potential increases having been attributed to the formation of quinone derivatives as noted above, the increase in peak fluorescence intensities is likely attributed to dimer formation which is corroborated by the increased stability of the aromatic ring due to pi-pi stacking also observed in the ATR-FTIR analysis. These results suggest that fluorescence spectroscopy may be used to monitor the heterogeneity of the manufactured PCR-PET films.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of optimizing a plastic composition formed from a plurality of resin feedstocks, said method comprising:
    providing a plurality of resin feedstocks;
    blending the plurality of resin feedstocks to form the plastic composition;
    measuring one or more properties of the plastic composition, wherein the one or more properties comprise one or more of radiation absorption, radiation transmission, gas evolution, or radiation fluorescence; and
    optimizing the radiation transmission, the radiation absorption, a radiation emission, or a radiation reflection by adjusting the ratio of the plurality of resin feedstocks being blended into the plastic composition, based on said measuring, to form an optimized plastic composition.

2. The method of claim 1, wherein the plastic composition comprises thermoplastic resin feedstocks.

3. The method of claim 2, wherein the thermoplastic resin feedstocks are polyethylene terephthalate (PET).

4. The method of claim 2, wherein the thermoplastic resin feedstocks are selected from the group consisting of polyethylene, polypropylene, polystyrene, poly methyl methacrylate, polycarbonate, an addition polymer, a condensation polymer, and mixtures thereof.

5. The method of claim 1, wherein the plurality of resin feedstocks comprise a recycled polymeric material and a virgin polymeric material.

6. The method of claim 5, wherein the recycled and virgin polymeric materials are polyethylene terephthalate (PET).

7. The method of claim 1, wherein the measuring is carried out, during said method, at least two different points in time following said blending.

8. The method of claim 1, wherein the measuring comprises one or more of an ultraviolet-visible spectroscopy analysis, an attenuated total reflectance Fourier transform infrared spectroscopy analysis, a mechanical analysis, x-ray fluorescence analysis, or energy dispersive x-ray fluorescence analysis.

9. The method of claim 1, wherein the radiation transmission, radiation absorption, radiation emission, or radiation reflection properties are optimized so the optimized plastic composition isolates and controls electromagnetic wavelengths associated with one or more of vitamin degradation, adverse color changes, chlorophyll degradation, or degradation of other nutritional components.

10. The method of claim 1, wherein said blending is carried out using a compound delivery system.

11. The method of claim 10, wherein the compound delivery system comprises one or more of a co-extruder, a dosing pump, or a direct intake to an extrusion line.

12. The method of claim 1 further comprising:
    adding, to the plastic composition, one or more additive compounds selected from the group consisting of thermal or light stabilizers, antioxidants, plasticizers, fillers, nucleating agents, colorants, thermal conductors, catalysts, and combinations thereof.

13. The method of claim 1, wherein said blending is carrier out to produce a plastic composition that absorbs 50% to 75% more incident ultraviolet light compared to composition feedstocks that do not contain recycled content.

* * * * *